(12) United States Patent
Ple

(10) Patent No.: US 7,462,623 B2
(45) Date of Patent: Dec. 9, 2008

(54) QUINAZOLINE DERIVATIVES AS SRC TYROSINE KINASE INHIBITORS

(75) Inventor: Patrick Ple, Reims (FR)

(73) Assignee: AstraZeneca AB, Sodertalje (SE)

( * ) Notice: Subject to any disclaimer, the term of this patent is extended or adjusted under 35 U.S.C. 154(b) by 551 days.

(21) Appl. No.: 10/533,931

(22) PCT Filed: Oct. 29, 2003

(86) PCT No.: PCT/GB03/04703

§ 371 (c)(1), (2), (4) Date: May 4, 2005

(87) PCT Pub. No.: WO2004/041829

PCT Pub. Date: May 21, 2004

(65) Prior Publication Data

US 2006/0122199 A1 Jun. 8, 2006

(30) Foreign Application Priority Data

Nov. 4, 2002 (EP) .................... 02292736
Apr. 10, 2003 (EP) .................... 03290900

(51) Int. Cl.
A61K 31/517 (2006.01)
C07D 239/94 (2006.01)

(52) U.S. Cl. .................. 514/266.21; 544/284
(58) Field of Classification Search ............ 514/266.21; 544/284

See application file for complete search history.

(56) References Cited

U.S. PATENT DOCUMENTS

| | | | | |
|---|---|---|---|---|
| 5,576,322 A | 11/1996 | Takase et al. | ......... | 514/266.22 |
| 5,580,870 A | 12/1996 | Barker et al. | ......... | 514/234.5 |
| 5,693,652 A | 12/1997 | Takase et al. | ......... | 514/322 |
| 5,801,180 A | 9/1998 | Takase et al. | ......... | 514/266.24 |
| 5,866,572 A * | 2/1999 | Barker et al. | ......... | 514/234.5 |
| 5,962,458 A | 10/1999 | Lohmann et al. | ......... | 514/266.21 |
| 6,046,206 A | 4/2000 | Pamukcu et al. | ......... | 514/266.21 |
| 6,071,921 A | 6/2000 | Lohmann et al. | ......... | 514/266.22 |
| 6,184,225 B1 | 2/2001 | Thomas et al. | ......... | 514/234.5 |
| 6,258,951 B1 | 7/2001 | Lohmann et al. | ......... | 544/283 |
| 6,265,411 B1 | 7/2001 | Thomas et al. | ......... | 514/266.2 |
| 6,291,455 B1 | 9/2001 | Thomas et al. | ......... | 514/231.5 |
| 6,294,532 B1 | 9/2001 | Thomas et al. | ......... | 514/228.2 |
| 6,362,336 B1 | 3/2002 | Lohmann et al. | ......... | 544/283 |
| 6,399,602 B1 * | 6/2002 | Barker et al. | ......... | 514/234.5 |
| 6,414,148 B1 | 7/2002 | Thomas et al. | ......... | 544/283 |
| 6,514,971 B1 | 2/2003 | Thomas et al. | ......... | 514/234.5 |
| 6,673,803 B2 | 1/2004 | Thomas et al. | ......... | 514/263.4 |
| 6,809,097 B1 | 10/2004 | Thomas et al. | ......... | 514/235.2 |
| 6,849,625 B2 | 2/2005 | Lambert et al. | ......... | 514/234.5 |
| 6,887,874 B2 | 5/2005 | Hennequin | ......... | 514/248 |
| 6,897,210 B2 | 5/2005 | Thomas et al. | ......... | 514/183 |
| 6,897,214 B2 * | 5/2005 | Barker et al. | ......... | 514/234.5 |
| 6,939,866 B2 | 9/2005 | Lambert et al. | ......... | 514/62 |
| 7,049,438 B2 | 5/2006 | Hennequin et al. | | |
| 7,074,800 B1 | 7/2006 | Hennequin et al. | | |
| 7,087,602 B2 | 8/2006 | Thomas et al. | | |
| 7,115,615 B2 * | 10/2006 | Hennequin et al. | ..... | 514/266.24 |
| 7,141,577 B2 | 11/2006 | Ple | | |
| 7,160,889 B2 | 1/2007 | Hennequin et al. | | |
| 7,173,038 B1 | 2/2007 | Thomas et al. | | |
| 7,262,201 B1 | 8/2007 | Hennequin et al. | | |
| 7,268,230 B2 | 9/2007 | Hennequin | | |
| 2006/0142297 A1 * | 6/2006 | Barge | .............. | 514/252.17 |
| 2006/0223815 A1 * | 10/2006 | Curwen et al. | ......... | 514/252.17 |

FOREIGN PATENT DOCUMENTS

| | | |
|---|---|---|
| EP | 0607439 | 1/2002 |
| EP | 0602851 | 10/2002 |
| WO | WO 92/20642 | 11/1992 |
| WO | 95/15758 | 6/1995 |
| WO | WO 95/15758 | 6/1995 |
| WO | WO 96/09294 | 3/1996 |
| WO | WO 96/39145 | 12/1996 |
| WO | 97/03069 | 1/1997 |
| WO | WO 97/03069 | 1/1997 |
| WO | WO 97/30035 | 8/1997 |
| WO | WO 97/32856 | 9/1997 |
| WO | WO 97/34876 | 9/1997 |

(Continued)

Primary Examiner—James O. Wilson
Assistant Examiner—Tamthom N Truong
(74) Attorney, Agent, or Firm—Morgan, Lewis & Bockius LLP

(57) ABSTRACT

The invention concerns quinazoline derivatives of Formula (I): (A chemical formula should be inserted here—please see paper copy enclosed herewith) wherein Z is an O, S, SO, $SO_2$, $N(R^2)$ or $C(R^2)_2$ group wherein each $R^2$ group is hydrogen or (1-8C) alkyl, m is 0, 1, 2 or 3, each $R^1$ group is selected from halogeno, (1-8C) alkyl, (1-6C) alkoxy and any of the other meanings defined in the description, n is 0, 1, 2 or 3, and each $R^3$ group is selected from halogeno, (1-8C) alkyl, (1-6C) alkoxy and any of the other meanings defined in the description, or pharmaceutically-acceptable salts thereof, processes for their preparation, pharmaceutical compositions containing them and their use in the manufacture of a medicament for use as an anti-invasive agent in the containment and/or treatment of solid tumor disease.

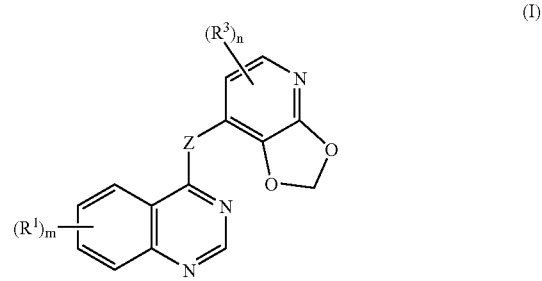

12 Claims, No Drawings

FOREIGN PATENT DOCUMENTS

| | | |
|---|---|---|
| WO | WO 97/42187 | 11/1997 |
| WO | WO 98/02434 | 1/1998 |
| WO | WO 98/13350 | 4/1998 |
| WO | WO 98/13354 | 4/1998 |
| WO | WO 99/10349 | 3/1999 |
| WO | WO 00/18761 | 4/2000 |
| WO | WO 00/21955 | 4/2000 |
| WO | WO 00/47212 | 8/2000 |
| WO | WO 01/21594 | 3/2001 |
| WO | WO 01/21597 | 3/2001 |
| WO | WO 01/32651 | 5/2001 |
| WO | WO 01/66099 | 9/2001 |
| WO | WO 01/74360 | 10/2001 |
| WO | WO 01/77085 | 10/2001 |
| WO | WO 01/94341 | 12/2001 |
| WO | 02/16352 | 2/2002 |
| WO | WO 02/12226 | 2/2002 |
| WO | WO 02/12227 | 2/2002 |
| WO | WO 02/12228 | 2/2002 |
| WO | WO 02/16352 | 2/2002 |
| WO | WO 02/30924 | 4/2002 |
| WO | WO 02/30926 | 4/2002 |
| WO | WO 92/34744 | 5/2002 |
| WO | WO 02/085895 | 10/2002 |
| WO | WO 02/092577 | 11/2002 |
| WO | WO 02/092578 | 11/2002 |
| WO | WO 02/092579 | 11/2002 |
| WO | WO 03/008409 | 1/2003 |
| WO | WO 03/039551 | 5/2003 |
| WO | WO 03/047582 | 6/2003 |
| WO | WO 03/064413 | 8/2003 |
| WO | WO 2004/004732 | 1/2004 |
| WO | WO 2004/005284 | 1/2004 |
| WO | WO 2004/014383 | 2/2004 |
| WO | WO 2004/014426 | 2/2004 |
| WO | WO 2004/032937 | 4/2004 |
| WO | WO 2004/043472 | 5/2004 |
| WO | WO 2004/071397 | 8/2004 |

* cited by examiner

QUINAZOLINE DERIVATIVES AS SRC TYROSINE KINASE INHIBITORS

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of peptides which are receptors for growth factors. Activation of the growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp60$^{v-Src}$ tyrosine kinase (otherwise known as v-Src), and the corresponding tyrosine kinases in normal cells, for example pp60$^{c-Src}$ tyrosine kinase (otherwise known as c-Src).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGF1 receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell*, 1990, 61, 203-212, Bolen et al., *FASEB J.*, 1992, 6, 3403-3409, Brickell et al., *Critical Reviews in Oncogenesis*, 1992, 3, 401-406, Bohlen et al., *Oncogene*, 1993, 8, 2025-2031, Courtneidge et al., *Semin. Cancer Biol.*, 1994, 5, 239-246, Lauffenburger et al., *Cell*, 1996, 84, 359-369, Hanks et al., *BioEssays*, 1996, 19, 137-145, Parsons et al., *Current Opinion in Cell Biology*, 1997, 9, 187-192, Brown et al., *Biochimica et Biophysica Acta*, 1996, 1287, 121-149 and Schlaepfer et al., *Progress in Biophysics and Molecular Biology*, 1999, 71, 435-478). Various classes of non-receptor tyrosine kinases are known including the Src family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, are frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558-562 and Mao et al., *Oncogene*, 1997, 15, 3083-3090), and breast cancer (Muthuswamy et al., *Oncogene*, 1995, 11, 1801-1810). The Src family of non-receptor tyrosine kinases has also been located in other common human cancers such as non-small cell lung cancers (NSCLCs) including adenocarcinomas and squamous cell cancer of the lung (Mazurenko et al., *European Journal of Cancer*, 1992, 28, 372-7), bladder cancer (Fanning et al., *Cancer Research*, 1992, 52, 1457-62), oesophageal cancer (Jankowski et al., *Gut*, 1992, 33, 1033-8), cancer of the prostate, ovarian cancer (Wiener et al., *Clin. Cancer Research*, 1999, 5, 2164-70) and pancreatic cancer (Lutz et al., *Biochem. and Biophys. Res. Comm.*, 1998, 243, 503-8). As further human tumour tissues are tested for the Src family of non-receptor tyrosine kinases it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51-64 and Klinghoffer et al., *EMBO Journal*, 1999, 18, 2459-2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283-293, Fincham et al., *EMBO J*, 1998, 17, 81-92 and Verbeek et al., *Exp. Cell Research*, 1999, 248, 531-537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by way of inhibition of the Src family of non-receptor tyrosine kinases, for example by inhibition of one or more of c-Src, c-Yes and c-Fyn.

It is also known that c-Src non-receptor tyrosine kinase enzyme is involved in the control of osteoclast-driven bone resorption (Soriano et al., *Cell*, 1991, 64, 693-702; Boyce et al., *J. Clin. Invest.*, 1992, 90, 1622-1627; Yoneda et al., *J. Clin. Invest.*, 1993, 91, 2791-2795 and Missbach et al., *Bone*, 1999, 24, 437-49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

Generally the compounds of the present invention possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase.

Furthermore, certain compounds of the present invention possess substantially better potency against the Src family of non-receptor tyrosine kinases, for example c-Src and/or c-Yes, than against VEGF receptor tyrosine kinase. Such compounds possess sufficient potency against the Src family of non-receptor tyrosine kinases, for example c-Src and/or c-Yes, that they may be used in an amount sufficient to inhibit, for example, c-Src and/or c-Yes whilst demonstrating little activity against VEGF receptor tyrosine kinase. It is advantageous to minimise VEGF receptor tyrosine kinase inhibitory activity as some compounds having that activity have been found to act as potassium channel blockers, for example in a human ether-a-go-go-related-gene (hERG)-encoded potassium channel assay. Such activity may give rise to electrocardiogram (ECG) changes in vivo.

The anti-cancer treatment defined hereinafter may be applied as a sole therapy or may involve, in addition to the quinazoline derivative of the invention, conventional surgery or radiotherapy or chemotherapy. It is well known that nearly all drugs are metabolised to some degree in the human, generally to a less lipid soluble compound which is more easily excreted by the kidney. Many of the drug metabolic enzymes are found in the endoplasmic reticulum (which form microsomes upon homogenisation) of hepatocytes. The liver is the major site of drug metabolism because the liver cells (hepatocytes) contain particularly high concentrations of drug metabolising enzymes. Cytochrome P450 is a family of isoenzymes found in hepatic microsomes. Six specific P450 isoenzymes are responsible for the metabolism of most of the commonly used drugs, namely P450 1A2, 2C9, 2C19, 2D6, 2E1 and 3A4. Combination chemotherapy can be problematic if one or more of the component drugs of the combination are metabolised by Cytochtome P450 3A4 (hereinafter CYP 3A4). Such a component may be a substrate for CYP 3A4 or it may be an inducer or an inhibitor of that isoenzyme. Such effects can affect the pharmacokinetics of the other component of the combination therapy.

We have established that certain compounds of the present invention have the advantageous property of being less liable to metabolism by such P450 isoenzymes, particularly by CYP 3A4. Accordingly, it is possible to administer such compounds in combination anti-cancer therapy with greater safety.

We have further established that certain compounds of the present invention are doubly advantageous in that they possess little activity against VEGF receptor tyrosine kinase and they show little or no tendency to be metabolised by P450 isoenzymes such as CYP 3A4.

It is stated in International Patent Application WO 01/94341 that a range of quinazoline derivatives are useful in the treatment of cancer. The compounds are stated to possess inhibitory activity against the Src family of non-receptor tyrosine kinases. There is the disclosure therein of certain 5-substituted quinazoline derivatives including certain 5-substituted 4-(2,3-methylenedioxyanilino)quinazolines. There is no disclosure therein of any 4-(2,3-methylenedioxypyrid-4-amino)quinazoline derivatives.

It is stated in International Patent Application WO 02/16352 that a range of 4-(2,3-methylenedioxyanilino) quinazoline derivatives are useful in the treatment of cancer. The compounds are stated to possess inhibitory activity against the Src family of non-receptor tyrosine kinases. There is no disclosure therein of any 4-(2,3-methylenedioxypyrid-4-ylamino)quinazoline derivatives.

According to one aspect of the invention there is provided a quinazoline derivative of the Formula I

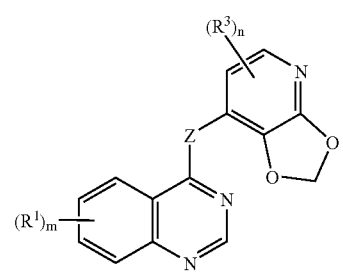

I wherein Z is an O, S, SO, $SO_2$, $N(R^2)$ or $C(R^2)_2$ group wherein each $R^2$ group, which may be the same or different, is hydrogen or (1-8C)alkyl;

m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$Q^1\text{-}X^1\text{—}$$

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1-8C)alkyl, and $Q^1$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1-8C)alkyl or, when the inserted group is $N(R^5)$, $R^5$ may also be (2-6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^2\text{-}X^2\text{—}$$

wherein $X^2$ is a direct bond or is selected from CO and $N(R^6)CO$, wherein $R^6$ is hydrogen or (1-8C)alkyl, and $Q^2$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno or (1-8C)alkyl substituents or a substituent selected from hydroxy, cyano, amino, carboxy, carbamoyl, oxo, thioxo, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$\text{—}X^3\text{-}Q^3$$

wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1-8C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a $R^1$ substituent optionally bears 1, 2 or 3 substituents, which may be the same or different, selected from halogeno, trifluoromethyl, cyano, nitro, hydroxy, amino, carboxy, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino and (1-3C)alkylenedioxy, or from a group of the formula:

$$\text{—}X^4\text{—}R^8$$

wherein $X^4$ is a direct bond or is selected from O and $N(R^9)$, wherein $R^9$ is hydrogen or (1-8C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, or from a group of the formula:

$$\text{—}X^5\text{-}Q^4$$

wherein $X^5$ is a direct bond or is selected from O, $N(R^{10})$ and CO, wherein $R^{10}$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-8C)alkyl, (2-8C)alkenyl, (2-8C)alkynyl and (1-6C)alkoxy, and wherein any heterocyclyl group within a $R^1$ substituent optionally bears 1 or 2 oxo or thioxo substituents;

n is 0, 1, 2 or 3; and each $R^3$ group, which may be the same or different, is selected from halogeno, trifluoromethyl, cyano, nitro, hydroxy, amino, carboxy, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$\text{—}X^6\text{—}R^{11}$$

wherein $X^6$ is a direct bond or is selected from O and $N(R^{12})$, wherein $R^{12}$ is hydrogen or (1-8C)alkyl, and $R^{11}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, or from a group of the formula:

$$\text{—}X^7\text{-}Q^5$$

wherein $X^7$ is a direct bond or is selected from O, S, SO, $SO_2$, $N(R^{13})$, CO, $CH(OR^{13})$, $CON(R^{13})$, $N(R^{13})CO$, $SO_2N(R^{13})$, $N(R^{13})SO_2$, $C(R^{13})_2O$, $C(R^{13})_2S$ and $N(R^{13})C(R^{13})_2$, wherein $R^{13}$ is hydrogen or (1-8C)alkyl, and $Q^5$ is aryl, aryl-(1-6C)alkyl, heteroaryl, heteroaryl-(1-6C)alkyl, heterocyclyl or heterocyclyl-1-6C)alkyl which optionally bears 1 or 2 substituents, which may be the same or different, selected from halogeno, (1-8C)alkyl, (2-8C)alkenyl, (2-8C)alkynyl and (1-6C)alkoxy, and any heterocyclyl group within $Q^5$ optionally bears 1 or 2 oxo or thioxo substituents;

or a pharmaceutically-acceptable salt thereof.

According to a further aspect of the invention there is provided a quinazoline derivative of the Formula I as defined hereinbefore wherein Z is O, S, SO, $SO_2$, $CH_2$ or NH;

m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$Q^1$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1-6C)alkyl, and $Q^1$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, or $(R^1)_m$ is (1-3C)alkylenedioxy, and wherein adjacent carbon atoms in any (2-6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1-6C)alkyl or, when the inserted group is $N(R^5)$, $R^5$ may also be (2-6C)alkanoyl, and wherein any $CH_2$=CH— or HC≡C— group within a $R^1$ substituent optionally bears at the terminal $CH_2$= or HC≡ position a substituent selected from halogeno, carboxy, carbamoyl, (1-6C)alkoxycarbonyl, N-(1-6C)alkylcarbamoyl, N,N-di-[(1-6C)alkyl]carbamoyl, amino(1-6C)alkyl, (1-6C)alkylamino-(1-6C)alkyl and di-[(1-6C)alkyl]amino-(1-6C)alkyl or from a group of the formula:

$Q^2$-$X^2$— wherein $X^2$ is a direct bond or is selected from CO and $N(R^6)CO$, wherein $R^6$ is hydrogen or (1-6C)alkyl, and $Q^2$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno or (1-6C)alkyl substituents or a substituent selected from hydroxy, cyano, amino, carboxy, carbamoyl, oxo, thioxo, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(7)_2$, wherein $R^7$ is hydrogen or (1-6C)alkyl, and $Q^3$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino and (1-3C)alkylenedioxy, or from a group of the formula:

—$X^4$—$R^8$ wherein $X^4$ is a direct bond or is selected from O and $N(R^9)$, wherein $R^9$ is hydrogen or (1-6C)alkyl, and $R^8$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, or from a group of the formula:

—$X^5$-$Q^4$ wherein $X^5$ is a direct bond or is selected from O, $N(R^{10})$ and CO, wherein $R^{10}$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and wherein any heterocyclyl group within a substituent on $R^1$ optionally bears 1 or 2 oxo or thioxo substituents;

n is 0, 1, 2 or 3; and each $R^3$ group, which may be the same or different, is selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino, N-(1-6C)alkyl-(3-6C)alkynoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

wherein $X^6$ is a direct bond or is selected from O and N($R^{12}$), wherein $R^{12}$ is hydrogen or (1-6C)alkyl, and $R^{11}$ is halogeno-(1-6C)alkyl, hydroxy-(1-6C)alkyl, (1-6C) alkoxy-(1-6C)alkyl, cyano-1-6C)alkyl, amino-(1-6C) alkyl, (1-6C)alkylamino-(1-6C)alkyl or di-[(1-6C) alkyl]amino-(1-6C)alkyl, or from a group of the formula:

wherein $X^7$ is a direct bond or is selected from O, S, SO, $SO_2$, N($R^{13}$), CO, CH(O$R^{13}$), CON($R^{13}$), N($R^{13}$)CO, $SO_2$N($R^{13}$), N($R^{13}$)$SO_2$, C($R^{13}$)$_2$O, C($R^{13}$)$_2$S and N($R^{13}$)C($R^{13}$)$_2$, wherein $R^{13}$ is hydrogen or (1-6C)alkyl, and $Q^5$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, (1-6C)alkyl, (2-8C)alkenyl, (2-8C)alkynyl and (1-6C)alkoxy, and any heterocyclyl group within $Q^5$ optionally bears 1 or 2 oxo or thioxo substituents;

or a pharmaceutically-acceptable salt thereof.

In this specification the generic term "alkyl" includes both straight-chain and branched-chain alkyl groups such as propyl, isopropyl and tert-butyl, and also (3-7C)cycloalkyl groups such as cyclopropyl, cyclobutyl, cyclopentyl, cyclohexyl and cycloheptyl, and also (3-7C)cycloalkyl-(1-2C) alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and (3-5C)cycloalkyl-(1-2C)alkoxy groups, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and (3-5C)cycloalkyl-(1-2C)alkylamino groups, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6C)alkyl]amino includes di-[(3-6C)cycloalkyl]amino groups and di-[(3-5C)cycloalkyl-(1-2C)alkyl]amino groups, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^5$) when it is aryl or for the aryl group within a 'Q' group is, for example, phenyl or naphthyl, preferably phenyl.

A suitable value for any one of the 'Q' groups ($Q^1$ or $Q^3$) when it is (3-7C)cycloalkyl or for the (3-7C)cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$ or $Q^3$) when it is (3-7C)cycloalkenyl or for the (3-7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^5$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^5$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C) alkyl, (3-7C)cycloalkyl-(1-6C)alkyl, (3-7C)cycloalkenyl-(1-6C)alkyl or heterocyclyl-(1-6C)alkyl group is present.

It is to be understood that there is a hydrogen atom at the 2-position on the quinazoline ring in structural Formula I. Thereby the $R^1$ substituents may only be located at the 5-, 6-, 7- or 8-positions on the quinazoline ring i.e. that the 2-position remains unsubstituted. It is further to be understood that the $R^3$ group that may be present on the 2,3-methylenedioxypyridyl group within structural Formula I may be located on either the 5- or 6-membered ring portions thereof, i.e. an $R^3$ group may be located on the pyridyl ring or on the methylene group within the 2,3-methylenedioxypyridyl group. For example, the $R^3$ group may be a methyl group that is located on the methylene group portion of the 2,3-methylenedioxypyridyl group i.e. the 2- and 3-positions on the pyridyl group bear an ethylidenedioxy group. Preferably, any $R^3$ group that is present on the 2,3-methylenedioxypyridyl group within structural Formula I is located on the pyridyl ring thereof. It is further to be understood that, when multiple $R^3$ groups are present, the $R^3$ groups may be the same or different.

Suitable values for any of the 'R' groups ($R^1$ to $R^{13}$) or for various groups within an $R^1$ or $R^3$ substituent include:—
for halogeno fluoro, chloro, bromo and iodo;
for (1-8C)alkyl: methyl, ethyl, propyl, isopropyl, tert-butyl, cyclobutyl, cyclopentyl and 2-cyclopropylethyl;
for (1-6C)alkyl: methyl, ethyl, propyl, isopropyl and tert-butyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulphinyl: methylsulphinyl and ethylsulphinyl;
for (1-6C)alkylsulphonyl: methylsulphonyl and ethylsulphonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl, propionyl and isobutyryl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N-(1-6C)alkylsulphamoyl: N-methylsulphamoyl and N-ethylsulphamoyl;
for N,N-di-[(1-6C)alkyl]sulphamoyl: N,N-dimethylsulphamoyl;
for (1-6C)alkanesulphonylamino: methanesulphonylamino and ethanesulphonylamino;
for N-(1-6C)alkyl-(1-6C)alkanesulphonylamino: N-methylmethanesulphonylamino and N-methylethanesulphonylamino;
for (3-6C)alkenoylamino: acrylamido, methacrylamido and crotonamido;
for N-(1-6C)alkyl-(3-6C)alkenoylamino: N-methylacrylamido and N-methylcrotonamido;
for (3-6C)alkynoylamino: propiolamido;
for N-(1-6C)alkyl-(3-6C)alkynoylamino: N-methylpropiolamido;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;
for halogeno-(1-6C)alkyl: chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl;
for hydroxy-(1-6C)alkyl: hydroxymethyl, 2-hydroxyethyl, 1-hydroxyethyl and 3-hydroxypropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for cyano-(1-6C)alkyl: cyanomethyl, 2-cyanoethyl, 1-cyanoethyl and 3-cyanopropyl;
for (2-6C)alkanoylamino-(1-6C)alkyl: acetamidomethyl, propionamidomethyl and 2-acetamidoethyl; and
for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1-3C)alkylenedioxy group or for a (1-3C)alkylenedioxy group within a $R^1$ substituent is, for example, methylenedioxy, ethylidenedioxy, isopropylidenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^1$ group. Similarly, when, for example a $CH_3$ group within a $R^1$ substituent bears a group of the formula —$X^3$-$Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q^2$-$X^2$— and —$X^7$-$Q^5$.

As defined hereinbefore, adjacent carbon atoms in any (2-6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^2$-$X^2$— wherein $X^2$ is, for example, NHCO and $Q^2$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent, optionally bears on each said $CH_2$ or $CH_3$ group one or more halogeno or (1-6C)alkyl substituents, there are suitably 1 or 2 halogeno or (1-6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted amino-(2-6C)alkoxy groups such as 3-amino-2-hydroxypropoxy, hydroxy-substituted (1-6C)

alkylamino-(2-6C)alkoxy groups such as 2-hydroxy-3-methylaminopropoxy, hydroxy-substituted di-[(1-6C)alkyl]amino-(2-6C)alkoxy groups such as 3-dimethylamino-2-hydroxypropoxy, hydroxy-substituted heterocyclyl-(1-6C)alkylamino groups such as 2-hydroxy-3-piperidinopropylamino and 2-hydroxy-3-morpholinopropylamino, hydroxy-substituted amino-(2-6C)alkylamino groups such as 3-amino-2-hydroxypropylamino, hydroxy-substituted (1-6C)alkylamino-(2-6C)alkylamino groups such as 2-hydroxy-3-methylaminopropylamino, hydroxy-substituted di-[(1-6C)alkyl]amino-(2-6C)alkylamino groups such as 3-dimethylamino-2-hydroxypropylamino, hydroxy-substituted (1-6C)alkoxy groups such as 2-hydroxyethoxy, (1-6C)alkoxy-substituted (1-6C)alkoxy groups such as 2-methoxyethoxy and 3-ethoxypropoxy, (1-6C)alkylsulphonyl-substituted (1-6C)alkoxy groups such as 2-methylsulphonylethoxy and heterocyclyl-substituted (1-6C)alkylamino-(1-6C)alkyl groups such as 2-morpholinoethylaminomethyl, 2-piperazin-1-ylethylaminomethyl and 3-morpholinopropylaminomethyl.

It is to be understood that when, as defined hereinbefore, any $CH_2$ or $CH_3$ group within a $R^1$ substituent optionally bears on each said $CH_2$ or $CH_3$ group a substituent as defined hereinbefore, such an optional substituent may be present on a $CH_2$ or $CH_3$ group within the hereinbefore defined substituents that may be present on an aryl, heteroaryl or heterocyclyl group within a $R^1$ substituent. For example, if $R^1$ includes an aryl or heteroaryl group that is substituted by a (1-8C)alkyl group, the (1-8C)alkyl group may be optionally substituted on a $CH_2$ or $CH_3$ group therein by one of the hereinbefore defined substituents therefor. For example, if $R^1$ includes a heteroaryl group that is substituted by, for example, a (1-6C)alkylamino-(1-6C)alkyl group, the terminal $CH_3$ group of the (1-6C)alkylamino group may be further substituted by, for example, a (1-6C)alkylsulphonyl group or a (2-6C)alkanoyl group. For example, the $R^1$ group may be a heteroaryl group such as a thienyl group that is substituted by a N-(2-methylsulphonylethyl)aminomethyl group such that $R^1$ is, for example, a 5-[N-(2-methylsulphonylethyl)aminomethyl]thien-2-yl group. Further, for example, if $R^1$ includes a heterocyclyl group such as a piperidinyl or piperazinyl group that is substituted on a nitrogen atom thereof by, for example, a (2-6C)alkanoyl group, the terminal $CH_3$ group of the (2-6C)alkanoyl group may be further substituted by, for example, a di-[(1-6C)alkyl]amino group. For example, the $R^1$ group may be a N-(2-dimethylaminoacetyl)piperidin-4-yl group or a 4-(2-dimethylaminoacetyl)piperazin-1-yl group.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the Formula I, or pharmaceutically-acceptable salts thereof, wherein, unless otherwise stated, each of Z, m, $R^1$, n and $R^3$ has any of the meanings defined hereinbefore or in paragraphs (a) to (o) hereinafter:—

(a) Z is O, S, SO, $SO_2$, $CH_2$ or NH;

(b) Z is O;

(c) Z is NH;

(d) m is 1 or 2, and each $R^1$ group, which may be the same or different, is selected from halogeno, trifluoromethyl, hydroxy, amino, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl, N,N-di-[(1-6C)alkyl]carbamoyl, (2-6C)alkanoylamino, N-(1-6C)alkyl-(2-6C)alkanoylamino, (3-6C)alkenoylamino, N-(1-6C)alkyl-(3-6C)alkenoylamino, (3-6C)alkynoylamino and N-(1-6C)alkyl-(3-6C)alkynoylamino, or from a group of the formula:

$$Q^1-X^1—$$

wherein $X^1$ is a direct bond or is selected from O, $N(R^4)$, $CON(R^4)$, $N(R^4)CO$ and $OC(R^4)_2$ wherein $R^4$ is hydrogen or (1-6C)alkyl, and $Q^1$ is aryl, aryl-(1-6C)alkyl, cycloalkyl-(1-6C)alkyl, heteroaryl, heteroaryl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, $N(R^5)$, $CON(R^5)$, $N(R^5)CO$, CH=CH and C≡C wherein $R^5$ is hydrogen or (1-6C)alkyl, or, when the inserted group is $N(R^5)$, $R^5$ may also be (2-6C)alkanoyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^2-X^2—$$

wherein $X^2$ is a direct bond or is CO or $N(R^6)CO$, wherein $R^6$ is hydrogen or (1-6C)alkyl, and $Q^2$ is heteroaryl, heteroaryl-(1-6C)alkyl, heterocyclyl or heterocyclyl-(1-6C)alkyl, and wherein any $CH_2$ or $CH_3$ group within a $R^1$ substituent optionally bears on each said $CH_2$ or $CH_3$ group one or more halogeno groups or a substituent selected from hydroxy, amino, oxo, (1-6C)alkoxy, (1-6C)alkylsulphonyl, (1-6C)alkylamino, di-[(1-6C)alkyl]amino, (2-6C)alkanoyloxy, (2-6C)alkanoylamino and N-(1-6C)alkyl-(2-6C)alkanoylamino, or from a group of the formula:

$$—X^3-Q^3$$

wherein $X^3$ is a direct bond or is selected from O, $N(R^6)$, $CON(R^7)$, $N(R^7)CO$ and $C(R^7)_2O$, wherein $R^7$ is hydrogen or (1-6C)alkyl, and $Q^3$ is heteroaryl, heteroaryl-(1-6C)alkyl, heterocyclyl or heterocyclyl-(1-6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-6C)alkyl, (2-8C)alkenyl, (2-8C)alkynyl, (1-6C)alkoxy, (1-6C)alkylsulphonyl, N-(1-6C)alkylcarbamoyl, N,N-di[(1-6C)alkyl]carbamoyl, (2-6C)alkanoyl and (1-3C)alkylenedioxy, or optionally bears 1 substituent selected from a group of the formula:

$$—X^4—R^8$$

wherein $X^4$ is a direct bond or is selected from O and $N(R^9)$, wherein $R^9$ is hydrogen or (1-6C)alkyl, and $R^8$ is halogeno-(1-6C)alkyl, hydroxy-(1-6C)alkyl, (1-6C)alkoxy-(1-6C)

alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl, and from a group of the formula:

$$-X^5-Q^4$$

wherein $X^5$ is a direct bond or is selected from O, N($R^{10}$) and CO, wherein $R^{10}$ is hydrogen or (1-6C)alkyl, and $Q^4$ is heterocyclyl or heterocyclyl-(1-6C)alkyl which optionally bears 1 or 2 substituents, which may be the same or different, selected from halogeno, (1-6C)alkyl and (1-6C)alkoxy, and wherein any heterocyclyl group within a substituent on $R^1$ optionally bears 1 or 2 oxo substituents;

(e) m is 1 or 2, and each $R^1$ group, which may be the same or different, is selected from fluoro, chloro, trifluoromethyl, hydroxy, amino, carbamoyl, methyl, ethyl, propyl, butyl, vinyl, allyl, but-3-enyl, pent-4-enyl, hex-5-enyl, ethynyl, 2-propynyl, but-3-ynyl, pent-4-ynyl, hex-5-ynyl, methoxy, ethoxy, propoxy, isopropoxy, butoxy, allyloxy, but-3-enyloxy, pent-4-enyloxy, hex-5-enyloxy, ethynyloxy, 2-propynyloxy, but-3-ynyloxy, pent-4-ynyloxy, hex-5-ynyloxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$$Q^1-X^1-$$

wherein $X^1$ is a direct bond or is selected from O, NH, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-(1,2,3,6-tetrahydropyridin-1-yl)ethyl, 3-(1,2,3,6-tetrahydropyridin-1-yl)propyl, 4-(1,2,3,6-tetrahydropyridin-1-yl)butyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2-6C)alkylene chain within a $R^1$ substituent are optionally separated by the insertion into the chain of a group selected from O, NH, N(Me), CONH, NHCO, CH=CH and C≡C, and wherein any CH$_2$=CH— or HC≡C— group within a $R^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl; 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$$Q^2-X^2-$$

wherein $X^2$ is a direct bond or is CO, NHCO or N(Me)CO and $Q^2$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin 4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a $R^1$ substituent optionally bears on each said CH$_2$ or CH$_3$ group one or more fluoro or chloro groups or a substituent selected from hydroxy, amino, oxo, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

$$-X^3-Q^3$$

wherein $X^3$ is a direct bond or is selected from O, NH, CONH, NHCO and CH$_2$O and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl, acetyl, propionyl, isobutyryl, methylenedioxy, ethylidenedioxy and isopropylidenedioxy, or optionally bears 1 substituent selected from a group of the formula:

$$-X^4-R^8$$

wherein $X^4$ is a direct bond or is selected from O and NH and $R^8$ is 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

$$-X^5-Q^4$$

wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(f) m is 1 and the $R^1$ group is located at the 5-, 6- or 7-position or m is 2 and the $R^1$ groups, which may be the same or different, are located at the 5- and 7-positions or at the 6- and 7-positions and each $R^1$ is selected from hydroxy, amino, methyl, ethyl, propyl, butyl, vinyl, ethynyl, methoxy, ethoxy, propoxy, isopropoxy, butoxy, pentyloxy, but-3-enyloxy, pent-4-enyloxy, hex-5-enyloxy, but-3-ynyloxy, pent-4-ynyloxy, hex-5-ynyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4$\underline{H}$-1,4-thiazinyl)ethoxy, 3-(1,1-dioxotetrahydro-4$\underline{H}$-1,4-thiazinyl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-1,2,3,6-tetrahydropyridin-1-yl)ethoxy 3-(1,2,3,6-tetrahydropyridin-1-yl)propoxy, 4-(1,2,3,6-tetrahydropyridin-1-yl)butoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4$\underline{H}$-1,4-thiazinyl)ethylamino, 3-(1,1-dioxotetrahydro-4$\underline{H}$-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, N(Me), CH=CH and C≡C, and when $R^1$ is a vinyl or ethynyl group, the $R^1$ substituent optionally bears at the terminal $CH_2$= or HC≡ position a substituent selected from $\underline{N}$-(2-dimethylaminoethyl)carbamoyl, $\underline{N}$-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^2-X^2—$$

wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group one or more fluoro or chloro groups or a substituent selected from hydroxy, oxo, amino, methoxy, methylsulphonyl, methylamino, dimethylamino, diisopropylamino, $\underline{N}$-ethyl-$\underline{N}$-methylamino, $\underline{N}$-isopropyl-$\underline{N}$-methylamino, $\underline{N}$-methyl-$\underline{N}$-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, ethoxy, N-methylcarbamoyl, N,N-dimethylcarbamoyl, methylenedioxy, ethylidendioxy and isopropylidenedioxy, and a pyrrolidin-2-yl, piperidin-3-yl, piperidin-4-yl, piperazin-1-yl or homopiperazin-1-yl group within a $R^1$ substituent is optionally $\underline{N}$-substituted with allyl, 2-propynyl, methylsulphonyl, ethylsulphonyl, acetyl, propionyl, isobutyryl, 2-fluoroethyl, 2,2-difluoroethyl, 2,2,2-trifluoroethyl, 3-fluoropropyl, 3,3-difluoropropyl, 3,3,3-trifluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(g) m is 1 and the $R^1$ group is located at the 7-position or m is 2 and the $R^1$ groups, which may be the same or different, are located at the 6- and 7-positions and each $R^1$ is selected from hydroxy, amino, methyl, ethyl, methoxy, ethoxy, propoxy, isopropoxy, butoxy, methylamino, ethylamino, dimethylamino, diethylamino, acetamido, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4$\underline{H}$-1,4-thiazin-4-yl)ethoxy, 3-(1,1-dioxotetrahydro-4$\underline{H}$-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2-6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents;

(h) m is 1 and the $R^1$ group is located at the 5-position or m is 2 and the $R^1$ groups, which may be the same or different, are located at the 5- and 7-positions and each $R^1$ is selected from hydroxy, amino, methyl, ethyl, methoxy, ethoxy, propoxy, isopropoxy, butoxy, methylamino, ethylamino, dimethylamino, diethylamino, acetamido, tetrahydrofuran-3-yloxy, tetrahydropyranyloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 3-piperidinyloxy, 4-piperidinyloxy, piperidin-3-ylmethoxy, piperidin-4-ylmethoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy, 3-homopiperazin-1-ylpropoxy, cyclobutyloxy, cyclopentyloxy and cyclohexyloxy, and wherein adjacent carbon atoms in any (2-6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents;

(i) m is 2 and the $R^1$ groups, which may be the same or different, are located at the 6- and 7-positions and the $R^1$ group at the 6-position is selected from hydroxy, methoxy, ethoxy and propoxy, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any $CH_2$ or $CH_3$ group within a $R^1$ substituent optionally bears on each said $CH_2$ or $CH_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents;

(j) m is 2 and the $R^1$ groups, which may be the same or different, are located at the 5- and 7-positions and the $R^1$ group at the 5-position is selected from methoxy, ethoxy, propoxy, isopropoxy, butoxy, tetrahydrofuran-3-yloxy, tetrahydropyran-4-yloxy, pyrrolidin-3-yloxy, pyrrolidin-2-ylmethoxy, 3-piperidinyloxy, 4-piperidinyloxy, piperidin-3-ylmethoxy, piperidin-4-ylmethoxy, cyclobutyloxy, cyclopentyloxy and cyclohexyloxy, and the $R^1$ group at the 7-position is selected from hydroxy, methoxy, ethoxy, propoxy, isopropoxy, butoxy, 2-pyrrolidin-1-ylethoxy, 3-pyrrolidin-1-ylpropoxy, 4-pyrrolidin-1-ylbutoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 2-piperidin-3-ylethoxy, 2-piperidin ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any $CH_2$ or $CH_3$ group within a $R^1$ substituent optionally bears on each said $CH_2$ or $CH_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents;

(k) n is 0;

(l) n is 1 or 2 and the $R^3$ groups, which may be the same or different, are located at the 5- and/or 6-positions of the 2,3-methylenedioxypyridin-4-yl group and are selected from halogeno, trifluoromethyl, cyano, hydroxy, (1-6C)alkyl, (2-8C)alkenyl, (2-8C)alkynyl and (1-6C)alkoxy;

(m) n is 1 or 2 and the $R^3$ groups, which may be the same or different, are located at the 5- and/or 6-positions of the 2,3-methylenedioxypyridin-4-yl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy;

(n) n is 0 or n is 1 and the $R^3$ group is located at the 5- or 6-position of the 2,3-methylenedioxypyridin-4-yl group, especially the 5-position, and is selected from fluoro, chloro, bromo, trifluoromethyl, cyano, hydroxy, methyl, ethyl, methoxy and ethoxy; and (o) n is 1 and the $R^3$ group is located at the 5-position of the 2,3-methylenedioxypyridin-4-yl group and is selected from fluoro, chloro, bromo, trifluoromethyl, cyano, hydroxy, methyl, ethyl, methoxy and ethoxy.

Further particular novel compounds of the invention include, for example, quinazoline derivatives of the Formula I, or pharmaceutically-acceptable salts thereof, wherein, unless otherwise stated, each of Z, m, $R^1$, n and $R^3$ has any of the meanings defined hereinbefore provided that:—

(A) $R^1$ substituents may only be located at the 5-, 6- and/or 7-positions on the quinazoline ring i.e. the 2- and 8-positions remain unsubstituted; or (B) $R^1$ substituents may only be located at the 6- and/or 7-positions on the quinazoline ring i.e. the 2-, 5- and 8-positions remain unsubstituted.

A particular compound of the invention is a quinazoline derivative of the Formula I wherein:

Z is O or NH;

m is 1 and the $R^1$ group is located at the 5-, 6- or 7-position or m is 2 and the $R^1$ groups, which may be the same or different, are located at the 5- and 7-positions or at the 6 and 7-positions and each $R^1$ is selected from hydroxy, amino, methyl, ethyl, propyl, butyl, vinyl, ethynyl, methoxy, ethoxy, propoxy, isopropoxy, butoxy, pentyloxy, but-3-enyloxy, pent-4-enyloxy, hex-5-enyloxy, but-3-ynyloxy, pent-4-ynyloxy, hex-5-ynyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-(1,2,3,6-tetrahydropyridin-1-yl)ethoxy 3-(1,2,3,6-tetrahydropyridin-1-yl)propoxy, 4-(1,2,3,6-tetrahydropyridin-1-yl)butoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2-6C)alkylene chain within a $R^1$ substituent are optionally separated by the insertion into the chain of a group selected from O, NH, N(Me), CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^2-X^2—$$

wherein $X^2$ is a direct bond or is NHCO or N(Me)CO and $Q^2$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a R$^1$ substituent optionally bears on each said CH$_2$ or CH$_3$ group one or more fluoro or chloro groups or a substituent selected from hydroxy, oxo, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on R$^1$ optionally bears 1 or 2 substituents, which may be the same or different, selected from fluoro, chloro, trifluoromethyl, hydroxy, amino, carbamoyl, methyl, ethyl, methoxy, ethoxy, N-methylcarbamoyl, N,N-dimethylcarbamoyl, methylenedioxy, ethylidendioxy and isopropylidenedioxy, and a pyrrolidin-2-yl, piperidin-3-yl, piperidinyl, piperazin-1-yl or homopiperazin-1-yl group within a R$^1$ substituent is optionally N-substituted with allyl, 2-propynyl, methylsulphonyl, ethylsulphonyl, acetyl, propionyl, isobutyryl, 2-fluoroethyl, 2,2-difluoroethyl, 2,2,2-trifluoroethyl, 3-fluoropropyl, 3,3-difluoropropyl, 3,3,3-trifluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on R$^1$ optionally bears 1 or 2 oxo substituents;

n is 0 or n is 1 and the R$^3$ group is located at the 5- or 6-position of the 2,3-methylenedioxypyridin-4-yl group and is selected from fluoro, chloro, bromo, trifluoromethyl, cyano, hydroxy, methyl, ethyl, methoxy and ethoxy; or a pharmaceutically-acceptable acid-addition salt thereof.

A further particular compound of the invention is a quinazoline derivative of the Formula I wherein:

Z is NH;

m is 2 and the R$^1$ groups, which may be the same or different, are located at the 6- and 7-positions and the R$^1$ group at the 6-position is selected from hydroxy, methoxy, ethoxy and propoxy, and the R$^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any CH$_2$ or CH$_3$ group within a R$^1$ substituent optionally bears on each said CH$_2$ or CH$_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on R$^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a R$^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on R$^1$ optionally bears 1 or 2 oxo substituents;

n is 0 or n is 1 and the R$^3$ group is located at the 5- or 6-position of the 2,3-methylenedioxypyridin-4-yl group and is selected from chloro, bromo, trifluoromethyl, cyano, hydroxy, methyl, ethyl, methoxy and ethoxy;

or a pharmaceutically-acceptable acid-addition salt thereof.

A further particular compound of the invention is a quinazoline derivative of the Formula I wherein:

Z is NH;

m is 2 and the first R$^1$ group is a 6-methoxy group and the second R$^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4 isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-chloroethoxy, 3-chloropropoxy, 4-chlorobutoxy, 2-methylsulphonylethoxy, 3-methylsulphonylpropoxy, 2-(2-methoxyethoxy)ethoxy, 2-(4-pyridyloxy)ethoxy, 3-pyridylmethoxy and 2-cyanopyrid-4-ylmethoxy; and n is 0 or n is 1 and the R$^3$ group is located at the 5- or 6-position of the 2,3-methylenedioxypyridin-4-yl group and is selected from fluoro, chloro, bromo, trifluoromethyl and cyano;

or a pharmaceutically-acceptable acid-addition salt thereof.

A further particular compound of the invention is a quinazoline derivative of the Formula I wherein:

Z is NH;

m is 2 and the first R$^1$ group is a 6-methoxy group and the second R$^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-piperidinoethoxy, 3-piperidinopropoxy, 2-(4-methylpiperazin-1-yl)ethoxy, 3-(4-methylpiperazin-1-yl)propoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 3-(4-acetylpiperazin-1-yl)propoxy, 2-(4-isobutyrylpiperazin-1-yl)ethoxy, 3-(4-isobutyrylpiperazin-1-yl)propoxy, 2-[4-(2,2,2-trifluoroethyl)piperazin-1-yl]ethoxy and 3-[4-(2,2,2-trifluoroethyl)piperazin-1-yl]propoxy; and n is 1 and the $R^3$ group is located at the 6-position of the 2,3-methylenedioxypyridin-4-yl group and is selected from chloro and bromo;

or a pharmaceutically-acceptable acid-addition salt thereof.

A further particular compound of the invention is a quinazoline derivative of the Formula I wherein:

Z is NH;

m is 2 and the $R^1$ groups, which may be the same or different, are located at the 5- and 7-positions and the $R^1$ group at the 5-position is selected from methoxy, ethoxy, propoxy, isopropoxy, butoxy, tetrahydrofuran-3-yloxy, tetrahydropyranyloxy, pyrrolidin-3-yloxy, pyrrolidin-2-ylmethoxy, 3-piperidinyloxy, 4-piperidinyloxy, piperidin-3-ylmethoxy, piperidin-4-ylmethoxy, cyclobutyloxy, cyclopentyloxy and cyclohexyloxy, and the $R^1$ group at the 7-position is selected from hydroxy, methoxy, ethoxy, propoxy, isopropoxy, butoxy, 2-pyrrolidin-1-ylethoxy, 3-pyrrolidin-1-ylpropoxy, 4-pyrrolidin-1-ylbutoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any $CH_2$ or $CH_3$ group within a $R^1$ substituent optionally bears on each said $CH_2$ or $CH_3$ group one or more chloro groups or a substituent selected from hydroxy, oxo, amino, methoxy, methylsulphonyl, methylamino, dimethylamino, diisopropylamino, N-ethyl-N-methylamino, N-isopropyl-N-methylamino and acetoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents;

n is 0 or n is 1 and the $R^3$ group is located at the 5- or 6-position of the 2,3-methylenedioxypyridin-4-yl group and is selected from fluoro, chloro, bromo, trifluoromethyl, cyano, hydroxy, methyl, ethyl, methoxy and ethoxy;

or a pharmaceutically-acceptable acid-addition salt thereof.

A further particular compound of the invention is a quinazoline derivative of the Formula I wherein:

Z is NH;

m is 1 and the $R^1$ group is located at the 5-position and is selected from ethoxy, propoxy, isopropoxy, butoxy, tetrahydrofuran-3-yloxy, tetrahydropyran-4-yloxy, tetrahydrothien-3-yloxy, 1,1-dioxotetrahydrothien-3-yloxy, tetrahydrothiopyran-4-yloxy, 1,1-dioxotetrahydrothiopyran-4-yloxy, N-methylazetidin-3-yloxy, N-ethylazetidin-3-yloxy, N-isopropylazetidin-3-yloxy, pyrrolidin-3-yloxy, N-methylpyrrolidin-3-yloxy, pyrrolidin-2-ylmethoxy, 3-piperidinyloxy, N-methylpiperidin-3-yloxy, 4-piperidinyloxy, N-methylpiperidin-4-yloxy, N-allylpiperidin-4-yloxy, N-prop-2-ynylpiperidin-4-yloxy, N-acetylpiperidin-4-yloxy, N-methylsulphonylpiperidin-4-yloxy, N-(2-methoxyethyl)piperidin-4-yloxy, piperidin-3-ylmethoxy, N-methylpiperidin-3-ylmethoxy, piperidin-4-ylmethoxy, N-methylpiperidin-4-ylmethoxy, cyclobutyloxy, cyclopentyloxy and cyclohexyloxy, or m is 2 and the first $R^1$ group is located at the 5-position and is selected from the group of substituents listed immediately above and the second $R^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4-isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-chloroethoxy, 3-chloropropoxy, 4-chlorobutoxy, 2-methylsulphonylethoxy, 3-methylsulphonylpropoxy, 2-(2-methoxyethoxy)ethoxy, 2-(4-pyridyloxy)ethoxy, 3-pyridylmethoxy and 2-cyanopyrid-4-ylmethoxy;

n is 0 or n is 1 and the $R^3$ group is located at the 5- or 6-position of the 2,3-methylenedioxypyridin-4-yl group and is selected from chloro, bromo, trifluoromethyl, cyano, hydroxy, methyl, ethyl, methoxy and ethoxy;

or a pharmaceutically-acceptable acid-addition salt thereof.

A further particular compound of the invention is a quinazoline derivative of the Formula I wherein:

Z is NH;

m is 1 and the $R^1$ group is located at the 5-position and is selected from propoxy, isopropoxy, tetrahydrofuran-3-yloxy, tetrahydropyranyloxy, pyrrolidin-3-yloxy, N-methylpyrrolidin-3-yloxy, pyrrolidin-2-ylmethoxy, 3-piperidinyloxy, N-methylpiperidin-3-yloxy, 4-piperidinyloxy, N-methylpiperidin-4-yloxy, N-allylpiperidin-4-yloxy, N-prop-2-ynylpiperidin-4-yloxy, N-acetylpiperidin-4-yloxy, N-methylsulphonylpiperidin-4-yloxy, piperidin-3-ylmethoxy, N-methylpiperidin-3-ylmethoxy, piperidin-4-ylmethoxy, N-methylpiperidin-4-ylmethoxy, cyclobutyloxy, cyclopentyloxy and cyclohexyloxy, or m is 2 and the first $R^1$ group is located at the 5-position and is selected from the group of substituents listed immediately above and the second $R^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4-isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-chloroethoxy, 3-chloropropoxy, 4-chlorobutoxy, 2-methylsulphonylethoxy, 3-methylsulphonylpropoxy, 2-(2-methoxyethoxy)ethoxy, 2-(4-pyridyloxy)ethoxy, 3-pyridylmethoxy and 2-cyanopyrid-4-ylmethoxy;

n is 0 or n is 1 and the $R^3$ group is located at the 5- or 6-position of the 2,3-methylenedioxypyridin-4-yl group and is selected from chloro, bromo, trifluoromethyl, cyano, hydroxy, methyl, ethyl, methoxy and ethoxy;

or a pharmaceutically-acceptable acid-addition salt thereof.

A further particular compound of the invention is a quinazoline derivative of the Formula I wherein:

Z is NH;

m is 1 and the $R^1$ group is located at the 5-position and is selected from propoxy, isopropoxy, tetrahydropyran-4-yloxy, 4-piperidinyloxy and N-methylpiperidin-4-yloxy, or m is 2 and the first $R^1$ group is located at the 5-position and is selected from the group of substituents listed immediately above, and the second $R^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 3-(4-acetylpiperazin-1-yl)propoxy, 2-(4-isobutyrylpiperazin-1-yl)ethoxy, 3-(4-isobutyrylpiperazin-1-yl)propoxy, 2-[4-(2,2,2-trifluoroethyl)piperazin-1-yl]ethoxy and 3-[4-(2,2,2-trifluoroethyl)piperazin-1-yl]propoxy; and n is 0 or n is 1 and the $R^3$ group is located at the 5- or 6-position of the 2,3-methylenedioxypyridin-4-yl group and is selected from fluoro, chloro, bromo, trifluoromethyl and cyano;

or a pharmaceutically-acceptable acid-addition salt thereof.

A further particular compound of the invention is a quinazoline derivative of the Formula I wherein:

Z is NH;

m is 2 and the first $R^1$ group is located at the 5-position and is selected from isopropoxy and tetrahydropyran-4-yloxy, and the second $R^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-piperidinoethoxy, 3-piperidinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 3-(4-acetylpiperazin-1-yl)propoxy, 2-(4-isobutyrylpiperazin-1-yl)ethoxy, 3-(4-isobutyrylpiperazin-1-yl)propoxy, 2-[4-(2-hydroxyethyl)piperazin-1-yl]ethoxy, 3-[4-(2-hydroxyethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-[4-(2-dimethylaminoacetyl)piperazin-1-yl]ethoxy and 3-[4-(2-dimethylaminoacetyl)piperazin-1-yl]propoxy; and n is 1 and the $R^3$ group is located at the 5-position of the 2,3-methylenedioxypyridin-4-yl group and is selected from chloro and bromo;

or a pharmaceutically-acceptable acid-addition salt thereof.

A further particular compound of the invention is a quinazoline derivative of the Formula I wherein:

Z is NH;

m is 2 and the first $R^1$ group is located at the 5-position and is selected from isopropoxy and tetrahydropyran-4-yloxy, and the second $R^1$ group is located at the 7-position and is selected from 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-piperidinoethoxy, 3-piperidinopropoxy, 2-(4-methylpiperazin-1-yl)ethoxy, 3-(4-methylpiperazin-1-yl)propoxy, 2-(4- allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 3-(4-acetylpiperazin-1-yl)propoxy, 2-(4-isobutyrylpiperazin-1-yl)ethoxy, 3-(4-isobutyrylpiperazin-1-yl)propoxy, 2-[4-(2,2,2-trifluoroethyl)piperazin-1-yl]ethoxy and 3-[4-(2,2,2-trifluoroethyl)piperazin-1-yl]propoxy; and n is 1 and the $R^3$ group is located at the 5-position of the 2,3-methylenedioxypyridin-4-yl group and is selected from chloro and bromo;

or a pharmaceutically-acceptable acid-addition salt thereof.

A further particular compound of the invention is a quinazoline derivative of the Formula I wherein:

Z is NH;

m is 2 and the first $R^1$ group is located at the 5-position and is selected from isopropoxy and tetrahydropyran-4-yloxy, and the second $R^1$ group is located at the 7-position and is selected from 2-pyrrolidin-1-ylethoxy, 2-[(3RS,4SR)-3,4-methylenedioxypyrrolidin-1-yl]ethoxy, 2-morpholinoethoxy, 3-morpholinopropoxy, 2-piperidinoethoxy, 2-piperazin-1-ylethoxy, 2-(4-methylpiperazin-1-yl)ethoxy, 2-(4-prop-2-ynylpiperazin-1-yl)ethoxy, 3-(4-prop-2-ynylpiperazin-1-yl)propoxy, 2-(4-acetylpiperazin-1-yl)ethoxy, 2-[4-(2-hydroxyethyl)piperazin-1-yl]ethoxy and 2-[4-(2-dimethylaminoacetyl)piperazin-1-yl]ethoxy; and n is 1 and the $R^3$ group is located at the 5-position of the 2,3-methylenedioxypyridin-4-yl group and is a chloro group;

or a pharmaceutically-acceptable acid-addition salt thereof.

A further particular compound of the invention is a quinazoline derivative of the Formula I wherein:

Z is NH;

m is 2 and the first $R^1$ group is located at the 5-position and is selected from isopropoxy and tetrahydropyran-4-yloxy, and the second $R^1$ group is located at the 7-position and is selected from 2-pyrrolidin-1-ylethoxy, 2-[(3RS,4SR)-3,4-methylenedioxypyrrolidin-1-yl]ethoxy, 2-morpholinoethoxy, 2-piperidinoethoxy, 2-piperazin-1-ylethoxy, 2-(4-methylpiperazin-1-yl)ethoxy, 2-(4-prop-2-ynylpiperazin-1-yl)ethoxy, 2-(4-acetylpiperazin-1-yl)ethoxy, 2-[4-(2-hydroxyethyl)piperazin-1-yl]ethoxy and 2-[4-(2-dimethylaminoacetyl)piperazin-1-yl]ethoxy; and n is 1 and the $R^3$ group is located at the 5-position of the 2,3-methylenedioxypyridin-4-yl group and is a chloro group;

or a pharmaceutically-acceptable acid-addition salt thereof.

A further particular compound of the invention is a quinazoline derivative of the Formula I wherein:

Z is NH;

m is 2 and the first $R^1$ group is a 5-isopropoxy group and the second $R^1$ group is located at the 7-position and is selected from 2-pyrrolidin-1-ylethoxy, 2-[(3RS,4SR)-3,4-methylenedioxypyrrolidin-1-yl]ethoxy, 2-morpholinoethoxy, 2-piperidinoethoxy, 2-piperazin-1-ylethoxy, 2-(4-methylpiperazin-1-yl)ethoxy, 2-(4-acetylpiperazin-1-yl)ethoxy and 2-[4-(2-hydroxyethyl)piperazin-1-yl]ethoxy; and n is 1 and the $R^3$ group is located at the 5-position of the 2,3-methylenedioxypyridin-4-yl group and is a chloro group;

or a pharmaceutically-acceptable acid-addition salt thereof.

A further particular compound of the invention is a quinazoline derivative of the Formula I wherein:

Z is NH;

m is 2 and the first $R^1$ group is a 5-isopropoxy group and the second $R^1$ group is located at the 7-position and is selected from 2-[(3RS,4SR)-3,4-methylenedioxypyrrolidin-1-yl]ethoxy, 2-piperazin-1-ylethoxy, 2-(4-methylpiperazin-1-yl)ethoxy, 2-(4-acetylpiperazin-1-yl)ethoxy and 2-[4-(2-hydroxyethyl)piperazin-1-yl]ethoxy; and n is 1 and the $R^3$ group is located at the 5-position of the 2,3-methylenedioxypyridin-4-yl group and is a chloro group;

or a pharmaceutically-acceptable acid-addition salt thereof.

Particular compounds of the invention are, for example, the quinazoline derivatives of the Formula I that are disclosed within Example 3, and Example 6(1) to 6(7) hereinafter.

A particular compound of the invention is, for example, a quinazoline derivative of the Formula I selected from:—

4-(5-chloro-2,3-methylenedioxypyrid-4-ylamino)-6-methoxy-7-[3-(4-prop-2-ynylpiperazin-1-yl)propoxy]quinazoline, 4-(5-chloro-2,3-methylenedioxypyrid-4-ylamino)-7-[3-(4-isobutyrylpiperazin-1-yl)propoxy]-6-methoxyquinazoline, 4-(5-chloro-2,3-methylenedioxypyrid-4-ylamino)-6-methoxy-7-{3-[4-(2,2,2-trifluoroethyl)piperazin-1-yl]propoxy}quinazoline and 4-(5-chloro-2,3-methylenedioxypyrid-4-ylamino)-6-methoxy-7-[2-(4-prop-2-ynylpiperazin-1-yl)ethoxy]quinazoline;

or a pharmaceutically-acceptable acid-addition salt thereof.

A further particular compound of the invention is, for example, a quinazoline derivative of the Formula I selected from:—

7-[2-(4-acetylpiperazin-1-yl)ethoxy]4-(5-chloro-2,3-methylenedioxypyrid-4-ylamino)-5-tetrahydropyran-4-yloxyquinazoline, 4-(5-chloro-2,3-methylenedioxypyrid-4-ylamino)-7-{2-[(3RS,4SR)-3,4-methylenedioxypyrrolidin-1-yl]ethoxy}-5-tetrahydropyran-4-yloxyquinazoline, 4-(5-chloro-2,3-methylenedioxypyrid-4-ylamino)-7-[2-(4-prop-2-ynylpiperazin-1-yl)ethoxy]-5-tetrahydropyran-4-yloxyquinazoline, 4-(5-chloro-2,3-methylenedioxypyrid-4-ylamino)-7-[3-(4-prop-2-ynylpiperazin-1-yl)propoxy]-5-tetrahydropyran-4-yloxyquinazoline, 4-(5-chloro-2,3-methylenedioxypyrid-4-ylamino)-7-(2-morpholinoethoxy)-5-tetrahydropyran-4-yloxyquinazoline and 4-(5-chloro-2,3-methylenedioxypyrid-4-ylamino)-7-(3-morpholinopropoxy)-5-tetrahydropyran-4-yloxyquinazoline;

or a pharmaceutically-acceptable acid-addition salt thereof.

A further particular compound of the invention is, for example, a quinazoline derivative of the Formula I selected from:—

7-[2-(4-acetylpiperazin-1-yl)ethoxy]4-(5-chloro-2,3-methylenedioxypyrid-4-ylamino)-5-isopropoxyquinazoline, 4-(5-chloro-2,3-methylenedioxypyrid-4-ylamino)-5-isopropoxy-7-(2-piperazin-1-ylethoxy)quinazoline, 4-(5-chloro-2,3-methylenedioxypyrid-4-ylamino)-7-{2-[4-(2-hydroxyethyl)piperazin-1-yl]ethoxy}-5-isopropoxyquinazoline, 4-(5-chloro-2,3-methylenedioxypyrid-4-ylamino)-5-isopropoxy-7-(2-pyrrolidin-1-ylethoxy)quinazoline, 4-(5-chloro-2,3-methylenedioxypyrid-4-ylamino)-5-isopropoxy-7-(2-piperidinoethoxy)quinazoline, 4-(5-chloro-2,3-methylenedioxypyrid-4-ylamino)-5-isopropoxy-7-(2-morpholinoethoxy)quinazoline, 4-(5-chloro-2,3-methylenedioxypyrid-4-ylamino)5-isopropoxy-7-(3-morpholinopropoxy)quinazoline, 4-(5-chloro-2,3-methylenedioxypyrid-4-ylamino)-5-isopropoxy-7-[2-(4-prop-2-ynylpiperazin-1-yl)ethoxy]quinazoline, 4-(5-chloro-2,3-methylenedioxypyrid-4-ylamino)-5-isopropoxy-7-[2-(4-methylpiperazin-1-yl)ethoxy]quinazoline and 4-(5-chloro-2,3-methylenedioxypyrid-4-ylamino)-7-{2-[4-(2-dimethylaminoacetyl)piperazin-1-yl]ethoxy}-5-isopropoxyquinazoline;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, m, $R^1$, Z, n and $R^3$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) For the production of those compounds of the Formula I wherein Z is an O, S or $N(R^2)$ group, the reaction of a quinazoline of the Formula II

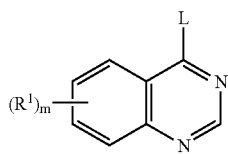

II wherein L is a displaceable group and m and $R^1$ have any of the meanings defined hereinbefore except that any functional group is protected if necessary, with a compound of the Formula III

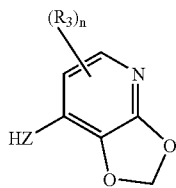

III wherein Z is O, S, or $N(R^2)$ and n, $R^3$ and $R^2$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 120° C.

Typically, the quinazoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

Quinazoline starting materials of the Formula II may be obtained by conventional procedures such as those disclosed in International Patent Applications WO 01/94341 and WO 02/16352. For example, a 1,4-dihydroquinolin-4-one of Formula IV

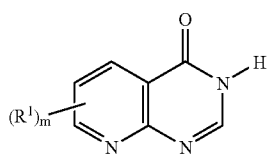

IV wherein m and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

4-Amino-2,3-methylenedioxypyridine starting materials (Formula III, for example when Z is NH) may be obtained by conventional procedures as illustrated in the Examples. Corresponding 4-hydroxy- and 4-mercapto-2,3-methylenedioxypyridine starting materials (Formula III, when Z is O or S respectively) may be obtained by conventional procedures.

(b) For the production of those compounds of the Formula I wherein at least one $R^1$ group is a group of the formula $Q^1$-$X^1$— wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^1$ is an oxygen atom, the coupling, conveniently in the presence of a suitable dehydrating agent, of a quinazoline of the Formula V

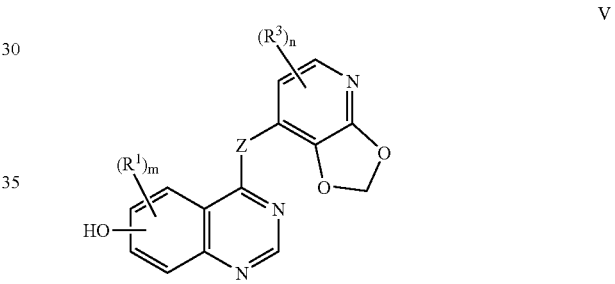

V wherein m, $R^1$, Z, n and $R^3$ have any of the meanings defined hereinbefore except that any functional group is protected if necessary, with an appropriate alcohol wherein any functional group is protected if necessary whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein an $R^1$ group contains a (1-6C)alkoxy or substituted (1-6C)alkoxy group or a (1-6C)alkylamino or substituted (1-6C)alkylamino group, the reaction, conveniently in the presence of a suitable base as defined hereinbefore, of a quinazoline derivative of the Formula VI

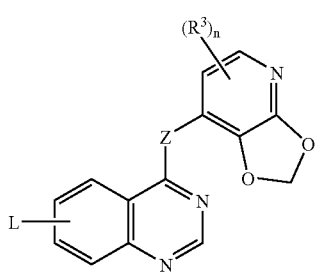

wherein L is a displaceable group as defined hereinbefore and Z, n and $R^3$ have any of the meanings defined hereinbefore except that any functional group is protected if necessary, with an alcohol or amine as appropriate whereafter any protecting group that is present is removed by conventional means.

The reaction is conveniently carried out in the presence of a suitable inert diluent or carrier as defined hereinbefore and at a temperature in the range 10 to 150° C., preferably at or near 50° C.

(d) For the production of those compounds of the Formula I wherein $R^1$ is an amino-substituted (1-6C)alkoxy group (such as a 2-(4-methylpiperazin-1-yl)ethoxy or 3-dimethylaminopropoxy group), the reaction of a compound of the Formula I wherein $R^1$ is a halogeno-substituted (1-6C)alkoxy group with a nitrogen-containing heterocyclyl compound or an appropriate amine.

The reaction is conveniently carried out in the presence of a suitable inert diluent or carrier as defined hereinbefore and at a temperature in the range 10 to 180° C., preferably in the range 60 to 120° C.

(e) For the production of those compounds of the Formula I wherein $R^1$ is an amino-hydroxy-disubstituted (1-6C)alkoxy group (such as 2-hydroxy-3-pyrrolidin-1-ylpropoxy or 3-[N-allyl-N-methylamino]-2-hydroxypropoxy), the reaction of a compound of the Formula I wherein the $R^1$ group contains an epoxy-substituted (1-6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(f) For the production of those compounds of the Formula I wherein Z is a SO or $SO_2$ group, the oxidation of a compound of Formula I wherein Z is a S group.

Conventional oxidation reagents and reaction conditions for such partial or complete oxidation of a sulphur atom are well known to the organic chemist.

(g) For the production of those compounds of the Formula I wherein an $R^1$ group contains an N-acylated heterocyclic group, the acylation, conveniently in the presence of a suitable base as defined hereinbefore, of a quinazoline derivative of the Formula I wherein the $R^1$ group contains a heterocyclic group having an unsubstituted NH group.

Suitable acylating agents are well known to the man skilled in the art and examples thereof are illustrated in the Examples. For example, a compound of the Formula I wherein a $R^1$ group contains a piperidinyl or piperazinyl group having an unsubstituted NH group may be reacted under conventional conditions with an optionally substituted carboxylic acid or a reactive derivative thereof.

A suitable reactive derivative of an optionally substituted carboxylic acid is, for example, a carboxylic acid halide; a carboxylic acid amide; a mixed anhydride, for example an anhydride formed by the reaction of the carboxylic acid and a chloroformate such as isobutyl chloroformate; the product of the reaction of the carboxylic acid with a carbodiimide such as dicyclohexylcarbodiimide or 1-(3-dimethylaminopropyl)-3-ethylcarbodiimide; the product of the reaction of the carboxylic acid with a mixture of an azo compound such as diethyl or di-tert-butyl azodicarboxylate and a phosphine such as triphenylphosphine; or the product of the reaction of the carboxylic acid with a uronium salt such as 2-(7-azabenzotriazol-1-yl)-1,1,3,3-tetramethyluronium hexafluorophosphate(V). For example, a suitable amino-substituted carboxylic acid is N,N-dimethylglycine and a suitable reactive derivative thereof is 2-dimethylaminoacetyl chloride.

The reaction is conveniently carried out in the presence of a suitable inert diluent or carrier as defined hereinbefore and at a temperature in the range 10 to 150° C., preferably at or near ambient temperature.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Many of the intermediates defined herein are novel and these are provided as a further feature of the invention. For example, many compounds of the Formula III

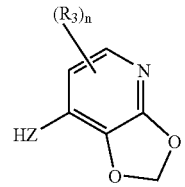

wherein Z is O, S, or $N(R^2)$ and n, $R^3$ and $R^2$ have any of the meanings defined hereinbefore are novel compounds. For example, although 4-amino-2,3-methylenedioxypyridine starting materials (Formula III, for example when Z is NH) may be obtained by conventional procedures as illustrated in the Examples, compounds such as 4-amino-5-chloro-2,3-methylenedioxypyridine is a novel compound which is provided as a further feature of the invention.

Biological Assays

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells, as inhibitors in vivo of the growth in nude mice of xenografts of A549 tissue, and for inhibition in vitro of the hERG-encoded potassium channel.

(a) In Vitro Enzyme Assay

The ability of test compounds to inhibit the phosphorylation of a tyrosine containing polypeptide substrate by the enzyme c-Src kinase was assessed using a conventional Elisa assay.

A substrate solution [100 μl of a 20 μg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 µM to 0.001 µM). Portions (25 µl) of each dilution of test compound were transferred to wells in the washed assay plates. "Total" control wells contained diluted DMSO instead of compound. Aliquots (25 µl) of an aqueous magnesium chloride solution (80 mM) containing adenosine-5′-triphosphate (ATP; 40 µM) was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 µl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 µl) was diluted by a factor of 1:6000 with PBST containing 0.5% w/v BSA and added to each well. The plates were incubated for 1 hour at ambient temperature. The supernatant liquid was discarded and each well was washed with PBST (×4). Horse radish peroxidase (HRP)-linked sheep anti-mouse Ig antibody (Amersham Catalogue No. NXA 931; 100 µl) was diluted by a factor of 1:500 with PBST containing 0.5% w/v BSA and added to each well. The plates were incubated for 1 hour at ambient temperature. The supernatant liquid was discarded and the wells were washed with PBST (×4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2′-azinobis(3-ethylbenzothiazoline-6-sulphonic acid) (ABTS; Boehringer Catalogue No. 1204 521). Aliquots (100 µl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro c-Src Transfected NIH 3T3 (c-Src 3T3) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., Cell, 1987, 49, 65-73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$:95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$:95% air) incubator.

BrdU labelling reagent (Boehringer Mannheim Catalogue No. 647 229) was diluted by a factor of 1:100 in DMEM medium containing 0.5% FCS and aliquots (20 µl) were added to each well to give a final concentration of 10 µM). The plates were incubated at 37° C. for 2 hours. The medium was decanted. A denaturating solution (FixDenat solution, Boehringer Mannheim Catalogue No. 647 229; 50 µl) was added to each well and the plates were placed on a plate shaker at ambient temperature for 45 minutes. The supernatant was decanted and the wells were washed with PBS (200 µl per well). Anti-BrdU-Peroxidase solution (Boehringer Mannheim Catalogue No. 647 229) was diluted by a factor of 1:100 in PBS containing 1% BSA and 0.025% dried skimmed milk (Marvel (registered trade mark), Premier Beverages, Stafford, GB) and an aliquot (100 µl) of the resultant solution was added to each well. The plates were placed on a plate shaker at ambient temperature for 90 minutes. The wells were washed with PBS (×5) to ensure removal of non-bound antibody conjugate. The plates were blotted dry and tetramethylbenzidine substrate solution (Boehringer Mannheim Catalogue No. 647 229; 100 µl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(c) In Vitro Microdroplet Migration Assay

This assay determines the ability of a test compound to inhibit the migration of adherent mammalian cell lines, for example the human tumour cell line A549.

RPMI medium (Sigma) containing 10% FCS, 1% L-glutamine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 µl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 µl) of medium which had been cooled to 4° C. were transferred into each well, taking care not to disturb the microdroplets. Test compounds were diluted from a 10 mM stock solution in DMSO using RPMI medium as described above. Aliquots (10 µl) of the diluted test compounds were transferred to the wells, again taking care not to disturb the microdroplets. The plates were incubated at 37° C. in a humidified (7.5% $CO_2$:95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(d) In Vivo A549 Xenograft Growth Assay

This test measures the ability of compounds to inhibit the growth of the A549 human carcinoma grown as a tumour in athymic nude mice (Alderley Park nu/nu strain). A total of about $5\times10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

(e) hERG-encoded Potassium Channel Assay

This assay determines the ability of a test compound to inhibit the tail current flowing through the hERG-encoded potassium channel.

Human embryonic kidney (HEK) cells expressing the hERG-encoded channel were grown in Eagle's Minimum Essential Medium (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at ambient temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/minute. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle. Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Cytochrome P450 isoenzyme assays may be conducted by conventional means.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):—

Test (a):—$IC_{50}$ in the range, for example, 0.001-10 µM;

Test (b):—$IC_{50}$ in the range, for example, 0.01-20 µM;

Test (c):—activity in the range, for example, 0.1-25 µM;

Test (d):—activity in the range, for example, 1-200 mg/kg/day.

In general, many of the particular compounds of the Formula I provided hereinafter as Examples possess activity at the following concentrations or doses in one or more of the above tests (a), (b), (c) and (d):—

Test (a):—$IC_{50}$ in the range, for example, 0.001-0.1 µM;
Test (b):—$IC_{50}$ in the range, for example, 0.01-1 µM;
Test (c):—activity in the range, for example, 0.1-1 µM;
Test (d):—activity in the range, for example, 1-200 mg/kg/day.

No physiologically-unacceptable toxicity was observed in Test (d) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

As stated above, it is known that the predominant role of c-Src non-receptor tyrosine kinase is to regulate cell motility which is necessarily required for a localised tumour to progress through the stages of dissemination into the blood stream, invasion of other tissues and initiation of metastatic tumour growth. We have found that the quinazoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Accordingly the quinazoline derivatives of the present invention are of value as anti-tumour agents, in particular as selective inhibitors of the motility, dissemination and invasiveness of mammalian cancer cells leading to inhibition of metastatic tumour growth. Particularly, the quinazoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment. Specifically, the compounds of the present invention are expected to be useful in the prevention or treatment of solid tumour disease.

Thus according to this aspect of the invention there is provided a quinazoline derivative of the Formula I, or a pharmaceutically-acceptable salt thereof, as defined hereinbefore for use as an anti-invasive agent in the containment and/or treatment of solid tumour disease.

According to a further feature of this aspect of the invention there is provided the use of a quinazoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of solid tumour disease in a warm-blooded animal such as man.

According to a further feature of this aspect of the invention there is provided a method for the prevention or treatment of solid tumour disease in a warm-blooded animal, such as man, in need of such treatment which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinazoline derivative of the Formula I, or a pharmaceutically-acceptable salt thereof, as defined hereinbefore.

According to a further aspect of the invention there is provided the use of a quinazoline derivative of the Formula I, or a pharmaceutically-acceptable salt thereof, as defined hereinbefore in the manufacture of a medicament for use in providing a c-Src kinase inhibitory effect.

The anti-cancer treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) other anti-invasion agents (for example metalloproteinase inhibitors like marimastat and inhibitors of urokinase plasminogen activator receptor function);

(ii) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(iii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iv) inhibitors of growth factor function, for example such inhibitors include growth factor antibodies, growth factor receptor antibodies (for example the anti-erbB2 antibody trastuzumab [Herceptin™] and the anti-erbB1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholino propoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of c-Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) where certain compounds were obtained as an acid-addition salt, for example a mono hydrochloride salt or a dihydrochloride salt, the stoichiometry of the salt was based on the number and nature of the basic groups in the compound, the exact stoichiometry of the salt was generally not determined, for example by means of elemental analysis data;

(xi) when describing the substituent on the amino group at the 4-position of the quinazoline ring in the Examples which follow, the following chemical nomenclature has been used '2,3-methylenedioxypyrid-4-yl' whereas, in the description and claims portions of the patent specification, that group is often described as a '2,3-methylenedioxypyridin-4-yl group'; for the avoidance of any doubt, it is to be understood that each of these terms relates to a group of formula

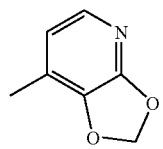

(x) the following abbreviations have been used:—
DMF N,N-dimethylformamide
DMSO dimethylsulphoxide
THF tetrahydrofuran
DMA N,N-dimethylacetamide

EXAMPLE 1

4-(5-chloro-2,3-methylenedioxypyrid-4-ylamino)-7-(3-chloropropoxy)-6-methoxyquinazoline Sodium hexamethyldisilazane (1M solution in THF; 0.734 ml) was added to a solution of 4-amino-5-chloro-2,3-methylenedioxypyridine (0.12 g) in DMF (4 ml) that had been cooled to 0° C. and the mixture was stirred for 15 minutes. A portion (0.1 g) of 4-chloro-7-(3-chloropropoxy)-6-methoxyquinazoline was added and the resultant mixture was stirred and allowed to warm to ambient temperature. The mixture was stirred at ambient temperature for 16 hours. The reaction mixture was evaporated and the residue was partitioned between methylene chloride and a saturated aqueous ammonium chloride solution. The organic phase was washed with water and with brine, dried over magnesium sulphate and evaporated. The residue was purified by column chromatography on silica using increasingly polar mixtures of methylene chloride and ethyl acetate as eluent followed by increasingly polar mixtures of methylene chloride and acetonitrile. There was thus obtained the title compound as a white foam (0.11 g); NMR Spectrum: (DMSOd$_6$ and CD$_3$CO$_2$D) 2.3 (m, 2H), 3.8 (m, 2H), 4.05 (s, 3H), 4.4 (t, 2H), 6.3 (s, 2H), 7.4 (s, 1H), 7.9 (s, 1H), 8.15 (s, 1H), 8.95 (s, 1H); Mass Spectrum: M+H$^+$ 423 and 425.

The 4-amino-5-chloro-2,3-methylenedioxypyridine used as a starting material was prepared as follows:—

Bromochloromethane (20 ml) was added to a mixture 5-chloro-2,3-dihydroxypyridine (30 g), caesium carbonate (100 g) and DMF (300 ml) and the mixture was stirred and heated to 90° C. for 3.5 hours. The mixture was cooled to ambient temperature and filtered. The filtrate was evaporated and the residue was purified by column chromatography on silica using methylene chloride as eluent. There was thus obtained 5-chloro-2,3-methylenedioxypyridine as a white solid (4.7 g); NMR Spectrum: (DMSOd$_6$) 6.25 (s, 2H), 7.5 (s, 1H), 7.65 (s, 1H).

A mixture of diisopropylamine (8.2 ml) and THF (100 ml) was cooled to −70° C. and n-butyllithium (2.5 M in hexane, 24 ml) was added dropwise. The mixture was stirred at −70° C. for a further 20 minutes. A solution of 5-chloro-2,3-methylenedioxypyridine (4.2 g) in THF (40 ml) was added over 10 minutes and the reaction mixture was stirred at −70° C. for 1 hour. Dry carbon dioxide gas was bubbled into the reaction mixture for 30 minutes. The resultant reaction mixture was allowed to warm to ambient temperature. Water (20 ml) was added and the organic solvent was evaporated. The residue was acidified to pH2 by the addition of 1N aqueous hydrochloric acid solution. The resultant solid was isolated and washed in turn with water and diethyl ether and dried under vacuum at 40° C. There was thus obtained 5-chloro-2,3-methylenedioxypyridine-4-carboxylic acid (3.6 g); $^{13}$C NMR Spectrum: (DMSOd$_6$) 103, 120, 121, 138, 140, 158, 163.

A mixture of the material so obtained, diphenylphosphoryl azide (3.6 ml), anhydrous tert-butanol (13.5 ml), triethylamine (4.2 ml) and 1,4-dioxane (63 ml) was stirred and heated to 100° C. for 3 hours. The mixture was evaporated and the residue was partitioned between ethyl acetate and water. The organic phase was washed with water, dried over magnesium sulphate and evaporated. The residue was purified by column chromatography on silica using a 9:1 mixture of methylene chloride and ethyl acetate as eluent. There was thus obtained tert-butyl 5-chloro-2,3-methylenedioxypyrid-4-ylcarbamate (3.8 g); NMR Spectrum: (DMSOd$_6$) 1.45 (s, 9H), 6.2 (s, 2H), 7.7 (s, 1H), 9.2 (s, 1H).

The material so obtained was dissolved in methylene chloride (35 ml) and the solution was cooled to 0° C. Trifluoroacetic acid (15 ml) was added and the mixture was stirred at 0° C. for 3 hours. The mixture was allowed to warm to ambient temperature and was stirred for 16 hours. The solvent was evaporated and the residue was diluted with ice water and neutralised to pH7 by the addition of 2N aqueous sodium hydroxide solution whilst keeping the mixture temperature at 0° C. The resultant mixture was extracted with methylene chloride and the extract dried over magnesium sulphate and evaporated. The residue was purified by column chromatography on silica using a 19:1 mixture of methylene chloride and diethyl ether as eluent. There was thus obtained 4-amino-5-chloro-2,3-methylenedioxypyridine (2 g); NMR Spectrum: (DMSOd$_6$) 6.1 (s, 2H), 6.2 (s, 2H), 7.45 (s, 1H); $^{13}$C NMR Spectrum: (DMSOd$_6$) 100, 112, 125, 136, 138, 157; Mass Spectrum: M+H$^+$ 173.

The 4-chloro-7-(3-chloropropoxy)-6-methoxyquinazoline used as a starting material was prepared as follows:—

Ammonium formate (45 g) was added portionwise over 1.25 hours to a stirred mixture of 7-benzyloxy-6-methoxy-3,4-dihydroquinazolin-4-one (International Patent Application WO 02/16352, Example 1 thereof; 20 g), 10% palladium-on-carbon catalyst (3.3 g) and DMF (530 ml) and the reaction mixture was stirred for an additional 30 minutes. The catalyst was removed by filtration and the solvent was evaporated. There was thus obtained 7-hydroxy-6-methoxy-3,4-dihydroquinazolin-4-one (8.65 g); NMR Spectrum: (DMSOd$_6$) 3.9 (s, 3H), 7.0 (s, 1H), 7.45 (s, 1H), 7.9 (s, 1H).

A mixture of the material so obtained, acetic anhydride (63 ml) and pyridine (7.5 ml) was heated to 100° C. for 4.5 hours. The resultant mixture was allowed to stand at ambient temperature for 16 hours. The mixture was poured into a stirred mixture (400 ml) of ice and water. The resultant precipitate was isolated and dried under vacuum. Analysis revealed that hydrolysis of the acetate group on the 4-position of the quinazoline was incomplete. The mixture was therefore further hydrolysed with water (150 ml) and pyridine (a few drops) at 90° C. for 15 minutes. The resultant mixture was cooled to ambient temperature and the solid was collected by filtration, washed with water and dried under vacuum. There was thus obtained 7-acetoxy-6-methoxy-3,4-dihydroquinazolin-4-one (7.4 g); NMR Spectrum: (DMSOd$_6$) 2.3 (s, 3H), 3.9 (s, 3H), 7.45 (s, 1H), 7.65 (s, 1H), 8.05 (s, 1H).

A mixture of a portion (2 g) of the material so obtained, thionyl chloride (32 ml) and DMF (5 drops) was stirred and heated to reflux for 1.5 hours. The mixture was cooled to ambient temperature and the excess of thionyl chloride was evaporated. Toluene was added to the residue and evaporated. The resultant residue was diluted with methylene chloride (15 ml) and a 10:1 mixture (80 ml) of methanol and a saturated aqueous ammonium hydroxide solution was added. The resultant mixture was stirred and heated to 80° C. for 10 minutes. The mixture was cooled to ambient temperature and evaporated. Water was added to the residue and the mixture was neutralised by the addition of dilute aqueous hydrochloric acid solution. The resultant precipitate was collected by filtration and dried under vacuum at 35° C. for 16 hours. There was thus obtained 4-chloro-7-hydroxy-6-methoxyquinazoline (1.65 g); NMR Spectrum: (DMSOd$_6$) 4.0 (s, 3H), 7.25 (s, 1H), 7.4 (s, 1H), 8.8 (s, 1H).

Di-tert-butyl azodicarboxylate (2.3 g) was added portionwise over a few minutes to a stirred mixture of 4-chloro-7-hydroxy-6-methoxyquinazoline (1.65 g), 3-chloropropanol (0.7 ml), triphenylphosphine (2.6 g) and methylene chloride (100 ml) and the reaction mixture was stirred at ambient temperature for 2 hours. The mixture was concentrated to a volume of about 30 ml by evaporation and the residue was purified by column chromatography on silica using increasingly polar mixtures of petroleum ether (b.p 40-60° C.) and ethyl acetate as eluent. There was thus obtained 4-chloro-7-(3-chloropropoxy)-6-methoxyquinazoline as a white solid (2 g); NMR Spectrum: (DMSOd$_6$) 2.3 (m, 2H), 3.8 (m, 2H), 4.05 (s, 3H), 4.4 (m, 2H), 7.45 (s, 1H), 7.55 (s, 1H), 8.9 (s, 1H).

EXAMPLE 2

7-(2-chloroethoxy)-4-(5-chloro-2,3-methylenedioxypyrid-4-ylamino)-6-methoxyquinazoline Using an analogous procedure to that described in Example 1, 4-chloro-7-(2-chloroethoxy)6-methoxyquinazoline was reacted with 4-amino-5-chloro-2,3-methylenedioxypyridine to give the title compound in 92% yield; NMR Spectrum: (DMSOd$_6$ and CD$_3$CO$_2$D) 4.05 (s, 3H), 4.1 (t, 2H), 4.55 (t, 2H), 6.3 (s, 2H), 7.4 (s, 1H), 7.9 (s, 1H), 8.15 (s, 1H), 8.95 (s, 1H); Mass Spectrum: M+H$^+$ 409 and 411.

The 4-chloro-7-(2-chloroethoxy)-6-methoxyquinazoline used as a starting material was prepared as follows:—

1,2-Dichloroethane (400 ml) was added to a stirred mixture of 7-hydroxy-6-methoxy-3-pivaloyloxymethyl-3,4-dihydroquinazolin-4-one (International Patent Application WO 02/16352, Example 2, Note [4] thereof; 85 g), potassium carbonate (77 g) and DMF (400 ml) and the reaction mixture was heated to 70° C. for 16 hours. The reaction mixture was cooled to ambient temperature and filtered. The filtrate was evaporated and the solid so obtained was washed with water and dried over phosphorus pentoxide at 50° C. The material so obtained was purified by column chromatography on silica using increasingly polar mixtures of methylene chloride and ethyl acetate as eluent. There was thus obtained 7-(2-chloroethoxy)-6-methoxy-3-pivaloyloxymethyl-3,4-dihydroquinazolin-4-one as a white solid (65.6 g); NMR Spectrum: (CDCl$_3$) 1.2 (s, 9H), 3.9 (t, 2H), 4.0 (s, 3H), 4.4 (t, 2H), 5.95 (s, 2H), 7.1 (s, 1H), 7.7 (s, 1H), 8.2 (s, 1H); Mass Spectrum: M+H$^+$ 369 and 371.

A mixture of the material so obtained and a saturated solution of ammonia gas in methanol (1.6 L) was stirred at ambient temperature for 2 days. The solvent was concentrated by evaporation to about one-fourth of the original volume and the precipitate was collected by filtration and washed with diethyl ether. There was thus obtained 7-(2-chloroethoxy)-6-methoxy-3,4-dihydroquinazolin-4-one as a white solid (44 g); NMR Spectrum: (DMSOd$_6$) 3.9 (s, 3H), 4.05 (t, 2H), 4.4 (t, 2H), 7.15 (s, 1H), 7.45 (s, 1H), 8.0 (s, 1H); Mass Spectrum: M+H$^+$ 255 and 257.

A mixture of a portion (5 g) of the material so obtained, thionyl chloride (28 ml) and DMF (0.7 ml) was stirred and heated to 80° C. for 1.5 hours. The excess of thionyl chloride was evaporated and toluene was added and evaporated. The residual solid was suspended in a mixture of ice and water and basified to pH7.5 by the addition of 2N aqueous sodium hydroxide solution followed by a saturated aqueous sodium bicarbonate solution. The resultant solid was collected by filtration, washed with water and diethyl ether and dried over over phosphorus pentoxide under vacuum. The material so obtained was purified by column chromatography on silica using increasingly polar mixtures of methylene chloride and acetonitrile as eluent. There was thus obtained 4-chloro-7-(2-chloroethoxy)-6-methoxyquinazoline (3.06 g); NMR Spectrum: (CDCl$_3$) 3.95 (t, 2H), 4.1 (s, 3H), 4.5 (t, 2H), 7.35 (s, 1H), 7.45 (s, 1H), 8.9 (s, 1H); Mass Spectrum: M+H$^+$ 273 and 275.

EXAMPLE 3

4-(5-chloro-2,3-methylenedioxypyrid-4-ylamino)-6-methoxy-7-[3-(4-prop-2-ynylpiperazin-1-yl)propoxy]quinazoline A mixture of 4-(5-chloro-2,3-methylenedioxypyrid-4-ylamino)-7-(3-chloropropoxy)-6-methoxyquinazoline (0.08 g), 1-prop-2-ynylpiperazine (0.047 g), potassium iodide (0.01 g) and DMA (2 ml) was stirred and heated to 80° C. for 3.5 hours. The solvent was evaporated and the residue was partitioned between methylene chloride and a saturated aqueous ammonium chloride solution. The organic phase was dried over magnesium sulphate and evaporated. The residue was purified by column chromatography on silica using a 19:1 mixture of methylene chloride and methanol and then a 9:1 mixture of methylene chloride and a saturated methanolic ammonia solution as eluent. The resulting gum was triturated under diethyl ether. There was thus obtained the title compound as a solid (0.066 g); NMR Spectrum: (DMSOd$_6$ and CF$_3$CO$_2$D) 2.3 (m, 2H), 3.2-3.6 (br m, 10H), 3.75 (s, 1H), 3.95 (br s, 2H), 4.0 (s, 3H), 4.35 (m, 2H), 6.3 (s, 2H), 7.4 (s, 1H), 7.9 (s, 1H), 8.15 (s, 1H), 8.95 (s, 1H); Mass Spectrum: M+H$^+$ 511 and 513.

The 1-prop-2-ynylpiperazine used as a starting material was prepared as follows:—

Propargyl bromide (80% solution in toluene; 40 ml) was added dropwise during 10 minutes to a stirred mixture of 1-tert-butoxycarbonylpiperazine (50 g), potassium carbonate (74.2 g) and acetonitrile (2 L) that had been cooled to 0° C. The mixture was stirred for 1.5 hours and allowed to warm to ambient temperature. The mixture was filtered and the filtrate was evaporated. The residue was purified by column chromatography on silica using increasingly polar mixtures of methylene chloride and ethyl acetate as eluent. There was thus obtained tert-butyl 4-prop-2-ynylpiperazine-1-carboxylate as an oil (45.5 g); NMR Spectrum: (CDCl$_3$) 1.4 (s, 9H), 2.2 (s, 1H), 2.45 (m, 4H), 3.3 (s, 2H), 3.45 (m, 4H).

A solution of the material so obtained in methylene chloride (100 ml) was added slowly to a solution of hydrogen chloride gas in 1,4-dioxane (4M, 450 ml). The reaction was slightly exothermic and a precipitate formed as carbon dioxide gas was evolved. The mixture was stirred at ambient temperature for 1 hour. The resultant mixture was evaporated and the residue was suspended in methylene chloride. A solution of ammonia gas in methanol (7M, 110 ml) was added and the mixture was stirred at ambient temperature for 15 minutes. The mixture was filtered and the filtrate was evaporated. An oil was obtained which crystallised on standing. There was thus obtained 1-prop-2-ynylpiperazine (23 g); NMR Spectrum: (CDCl$_3$) 2.2 (s, 1H), 2.5 (br s, 4H), 2.85 (m, 4H), 3.25 (s, 2H).

EXAMPLE 4

7-(2-chloroethoxy)-4-(5-chloro-2,3-methylenedioxypyrid-4-ylamino)-5-tetrahydropyran-4-yloxyquinazoline Using an analogous procedure to that described in Example 1, 4-chloro-7-(2-chloroethoxy)-5-tetrahydropyran-4-yloxyquinazoline was reacted with 4-amino-5-chloro-2,3-methylenedioxypyridine to give the title compound in 37% yield; NMR Spectrum: (CDCl$_3$) 2.0 (m, 2H), 2.3 (m, 2H), 3.65 (m, 2H), 3.9 (m, 2H), 4.1 (m, 2H), 4.4 (m, 2H), 4.8 (m, 1H), 6.2 (s, 2H), 6.65 (s, 1H), 6.9 (s, 1H), 7.8 (s, 1H), 8.6 (s, 1H), 9.5 (s, 1H); Mass Spectrum: M+H$^+$ 479 and 481.

The 4-chloro-7-(2-chloroethoxy)-5-tetrahydropyran-4-yloxyquinazoline used as a starting material was prepared as follows:—

Di-tert-butyl azodicarboxylate (0.338 g) was added to a stirred mixture of 4-chloro-7-hydroxy-5-tetrahydropyran-4-yloxyquinazoline (International Patent Application WO 01/94341, Example 15, Note [10] thereof; 0.25 g), 2-chloroethanol (0.073 ml), triphenylphosphine (0.385 g) and methylene chloride (15 ml) and the reaction mixture was stirred at ambient temperature for 1 hour. The mixture was concentrated to a volume of about 5 ml by evaporation and the residue was purified by column chromatography on silica using increasingly polar mixtures of petroleum ether (b.p 40-60° C.) and ethyl acetate as eluent. There was thus obtained 4-chloro-7-(2-chloroethoxy)-5-tetrahydropyran-4-yloxyquinazoline as a solid (0.17 g); NMR Spectrum: (CDCl$_3$) 2.0 (m, 2H), 2.15 (m, 2H), 3.7 (m, 2H), 3.95 (t, 2H), 4.1 (m, 2H), 4.4 (t, 2H), 4.8 (m, 1H), 6.7 (s, 1H), 6.95 (s, 1H), 8.85 (s, 1H).

EXAMPLE 5

7-(2-chloroethoxy)-4-(5-chloro-2,3-methylenedioxypyrid-4-ylamino)-5-isopropoxyquinazoline Using an analogous procedure to that described in Example 1, 4-chloro-7-(2-chloroethoxy)-5-isopropoxyquinazoline was reacted with 4-amino-5-chloro-2,3-methylenedioxypyridine to give the title compound in 86% yield; NMR Spectrum: (CDCl$_3$) 1.55 (d, 6H), 3.9 (t, 2H), 4.4 (t, 2H), 4.9 (m, 1H), 6.2 (s, 2H), 6.6 (s, 1H), 6.85 (s, 1H), 7.75 (s, 1H), 8.6 (s, 1H), 9.65 (s, 1H); Mass Spectrum: M+H$^+$ 437 and 439.

The 4-chloro-7-(2-chloroethoxy)-5-isopropoxyquinazoline used as a starting material was prepared as follows:—

Di-tert-butyl azodicarboxylate (28.9 g) was added to a stirred mixture of 7-benzyloxy-5-hydroxy-3-pivaloyloxymethyl-3,4-dihydroquinazolin-4-one (International Patent Application WO 01/94341, Example 15, Note [8] thereof; 30 g), isopropanol (7.3 ml), triphenylphosphine (32.95 g) and methylene chloride (350 ml) that had been cooled to 0° C. The reaction mixture was allowed to warm to ambient temperature and was stirred for 1.5 hours. The mixture was evaporated and the residue was purified by column chromatography on silica using increasingly polar mixtures of methylene chloride and methanol as eluent. There was thus obtained 7-benzyloxy-5-isopropoxy-3,4-dihydroquinazolin-4-one as a solid (23.8 g); NMR Spectrum: (DMSOd$_6$) 7.89 (s, 1H), 7.5-7.3 (m, 5H), 6.75 (s, 1H), 6.62 (s, 1H), 5.24 (s, 2H), 4.65 (m, 1H), 1.29 (d, 6H).

Ammonium formate (48.4 g) was added to a stirred mixture of 7-benzyloxy-5-isopropoxy-3,4-dihydroquinazolin-4-one (23.8 g), 10% palladium-on-carbon catalyst (2.8 g) and DMF (300 ml) and the resultant mixture was stirred at ambient temperature for 2 hours. The mixture was filtered and the filtrate was evaporated. The material so obtained was triturated under water, the pH of which was adjusted to pH7. The solid so obtained was collected by filtration, washed with water and with diethyl ether and dried over phosphorus pentoxide under vacuum. There was thus obtained 7-hydroxy-5-isopropoxy-3,4-dihydroquinazolin-4-one as a white solid (15.9 g); NMR Spectrum: (DMSOd$_6$) 1.3 (d, 6H), 4.57 (m, 1H), 6.42 (s, 1H), 6.5 (s, 1H), 7.8 (s, 1H).

A mixture of the material so obtained, acetic anhydride (34 ml) and pyridine (0.62 ml) was heated to 70° C. for 30 minutes. The reaction mixture was cooled to ambient temperature and the excess of acetic anhydride was evaporated. The white solid so obtained was added to hot water (80° C., 250 ml) and the mixture was stirred vigorously and heated to 80° C. for 20 minutes. The mixture was cooled to ambient temperature and the solid was isolated and dried over phosphorus pentoxide. There was thus obtained 7-acetoxy-5-isopropoxy-3,4-dihydroquinazolin-4-one (17.86 g); NMR Spectrum: (DMSOd$_6$) 7.97 (s, 1H), 6.91 (s, 1H), 6.85 (s, 1H), 4.65 (m, 1H), 2.32 (s, 3H), 1.33 (d, 6H).

A mixture of a portion (5.4 g) of the material so obtained, triphenylphosphine (10.8 g), carbon tetrachloride (12 ml) and 1,2-dichloroethane (50 ml) was stirred and heated to 70° C. for 2 hours. The mixture was cooled to ambient temperature and the solvent was evaporated. The residue was dissolved in a 0.5M solution of ammonia gas in 1,4-dioxane (250 ml) and the mixture was heated to 70° C. for 10 minutes. The solvent was evaporated and the residue was cooled in an ice-water bath. Methylene chloride and water were added and the aqueous layer was brought to pH7 by the addition of dilute aqueous hydrochloric acid. The mixture was filtered. The organic phase was dried over magnesium sulphate and evaporated to give 4-chloro-7-hydroxy-5-isopropoxyquinazoline as a foam which was used without further purification.

Di-tert-butyl azodicarboxylate (7.9 g) was added to a stirred mixture of the 4-chloro-7-hydroxy-5-isopropoxyquinazoline so obtained, 2-chloroethanol (1.5 ml), triphenylphosphine (8 g) and methylene chloride (200 ml) and the reaction mixture was stirred at ambient temperature for 4 hours. The mixture was concentrated by evaporation and the residue was purified by column chromatography on silica using increasingly polar mixtures of petroleum ether (b.p 40-60° C.) and ethyl acetate as eluent. There was thus obtained 4-chloro-7-(2-chloroethoxy)-5-isopropoxyquinazoline (2.5 g); NMR Spectrum: (CDCl$_3$) 1.45 (d, 6H), 3.9 (t, 2H), 4.4 (t, 2H), 4.75 (m, 1H), 6.65 (s, 1H), 6.9 (s, 1H), 8.8 (s, 1H).

EXAMPLE 6

Using an analogous procedure to that described in Example 3, the appropriate 7-haloalkoxyquinazoline was reacted with the appropriate heterocyclic compound to give the compounds described in Table I. Unless otherwise stated, each compound described in Table I was obtained as a free base.

TABLE I

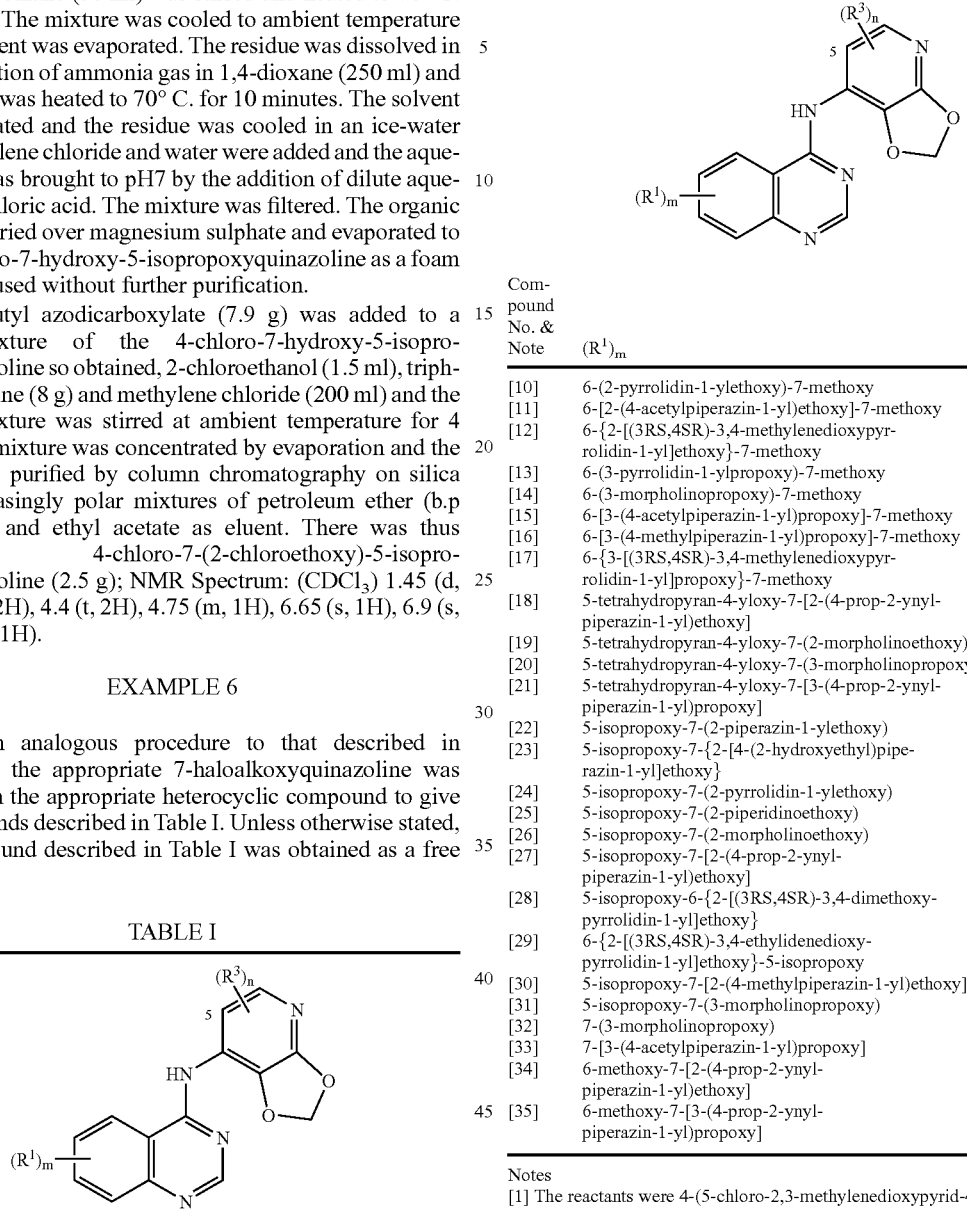

| Compound No. & Note | $(R^1)_m$ | $(R^3)_n$ |
|---|---|---|
| [1] | 6-methoxy-7-[3-(4-isobutyrylpiperazin-1-yl)propoxy] | 5-chloro |
| [2] | 6-methoxy-7-{3-[4-(2,2,2-trifluoroethyl)piperazin-1-yl]propoxy} | 5-chloro |
| [3] | 6-methoxy-7-[2-(4-prop-2-ynyl-piperazin-1-yl)ethoxy] | 5-chloro |
| [4] | 5-tetrahydropyran-4-yloxy-7-[2-(4-acetyl-piperazin-1-yl)ethoxy] | 5-chloro |
| [5] | 5-tetrahydro-pyran-4-yloxy-7-{2-[(3RS,4SR)-3,4-methylenedioxypyrrolidin-1-yl]ethoxy} | 5-chloro |
| [6] | 5-isopropoxy-7-[2-(4-acetylpiperazin-1-yl)ethoxy] | 5-chloro |
| [7] | 5-isopropoxy-7-{2-[(3RS,4SR)-3,4-methylenedioxypyrrolidin-1-yl]ethoxy} | 5-chloro |
| [8] | 6-(2-morpholinoethoxy)-7-methoxy | 5-chloro |
| [9] | 6-[2-(4-methylpiperazin-1-yl)ethoxy]-7-methoxy | 5-chloro |
| [10] | 6-(2-pyrrolidin-1-ylethoxy)-7-methoxy | 5-chloro |
| [11] | 6-[2-(4-acetylpiperazin-1-yl)ethoxy]-7-methoxy | 5-chloro |
| [12] | 6-{2-[(3RS,4SR)-3,4-methylenedioxypyrrolidin-1-yl]ethoxy}-7-methoxy | 5-chloro |
| [13] | 6-(3-pyrrolidin-1-ylpropoxy)-7-methoxy | 5-chloro |
| [14] | 6-(3-morpholinopropoxy)-7-methoxy | 5-chloro |
| [15] | 6-[3-(4-acetylpiperazin-1-yl)propoxy]-7-methoxy | 5-chloro |
| [16] | 6-[3-(4-methylpiperazin-1-yl)propoxy]-7-methoxy | 5-chloro |
| [17] | 6-{3-[(3RS,4SR)-3,4-methylenedioxypyrrolidin-1-yl]propoxy}-7-methoxy | 5-chloro |
| [18] | 5-tetrahydropyran-4-yloxy-7-[2-(4-prop-2-ynyl-piperazin-1-yl)ethoxy] | 5-chloro |
| [19] | 5-tetrahydropyran-4-yloxy-7-(2-morpholinoethoxy) | 5-chloro |
| [20] | 5-tetrahydropyran-4-yloxy-7-(3-morpholinopropoxy) | 5-chloro |
| [21] | 5-tetrahydropyran-4-yloxy-7-[3-(4-prop-2-ynyl-piperazin-1-yl)propoxy] | 5-chloro |
| [22] | 5-isopropoxy-7-(2-piperazin-1-ylethoxy) | 5-chloro |
| [23] | 5-isopropoxy-7-{2-[4-(2-hydroxyethyl)piperazin-1-yl]ethoxy} | 5-chloro |
| [24] | 5-isopropoxy-7-(2-pyrrolidin-1-ylethoxy) | 5-chloro |
| [25] | 5-isopropoxy-7-(2-piperidinoethoxy) | 5-chloro |
| [26] | 5-isopropoxy-7-(2-morpholinoethoxy) | 5-chloro |
| [27] | 5-isopropoxy-7-[2-(4-prop-2-ynyl-piperazin-1-yl)ethoxy] | 5-chloro |
| [28] | 5-isopropoxy-6-{2-[(3RS,4SR)-3,4-dimethoxy-pyrrolidin-1-yl]ethoxy} | 5-chloro |
| [29] | 6-{2-[(3RS,4SR)-3,4-ethylidenedioxy-pyrrolidin-1-yl]ethoxy}-5-isopropoxy | 5-chloro |
| [30] | 5-isopropoxy-7-[2-(4-methylpiperazin-1-yl)ethoxy] | 5-chloro |
| [31] | 5-isopropoxy-7-(3-morpholinopropoxy) | 5-chloro |
| [32] | 7-(3-morpholinopropoxy) | 5-chloro |
| [33] | 7-[3-(4-acetylpiperazin-1-yl)propoxy] | 5-chloro |
| [34] | 6-methoxy-7-[2-(4-prop-2-ynyl-piperazin-1-yl)ethoxy] | hydrogen |
| [35] | 6-methoxy-7-[3-(4-prop-2-ynyl-piperazin-1-yl)propoxy] | hydrogen |

Notes
[1] The reactants were 4-(5-chloro-2,3-methylenedioxypyrid-4-ylamino)-7-(3-chloropropoxy)-6-methoxyquinazoline and 1-isobutyrylpiperazine. The reaction mixture was heated to 120° C. for 3 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The material so obtained was dissolved in methylene chloride and an ion exchange resin (diethylaminopolystyrene resin, 4 equivalents) was added and the mixture was stirred for 30 minutes. The mixture was filtered and the filtrate was evaporated. The resultant residue was triturated under pentane to give the required product in 51% yield which gave the following characterising data; NMR Spectrum: (CDCl$_3$1.1(d, 6H), 2.1(m, 2H), 2.45(m, 4H), 2.55(m, 2H), 2.75(m, 1H), 3.5(m, 2H), 3.6(m, 2H), 4.0(s, 3H), 4.25(t, 2H), 6.1(s, 2H), 7.1(br s, 1H), 7.3(s, 1H), 7.75(s, 1H), 8.7(br s, 1H); Mass Spectrum: M + H$^+$ 543 and 545.

The 1-isobutyrylpiperazine used as a starting material was prepared as follows:—

Isobutyryl chloride (3.25 ml) was added dropwise to a stirred mixture of 1-benzylpiperazine (5 g), triethylamine (4.35 ml) and methylene chloride (75 ml) which was cooled to 0° C. The reaction mixture was allowed to warm to ambient temperature and stirred for 1 hour. The mixture was partitioned between methylene chloride and water. The organic phase was washed with water and with brine, dried over magnesium sulphate and evaporated. The residue was purified by column chromatography on silica using a 3:2 mixture of methylene chloride and ethyl acetate as eluent. There was thus obtained 1-benzyl-4-isobutyrylpiperazine (5.95 g) as an oil; NMR Spectrum: (CDCl$_3$) 1.1 (d, 6H), 2.45 (m, 4H), 2.8 (m, 1H), 3.5 (m, 4H), 3.65 (m, 2H), 7.3 (m, 5H); Mass Spectrum: M+H$^+$ 247.

A mixture of the material so obtained, cyclohexene (70 ml), palladium oxide-on-carbon catalyst (20%; 1.1 g) and ethanol (120 ml) was stirred and heated to 80° C. for 3 hours. The catalyst was removed by filtration and the solvent was evaporated to give 1-isobutyrylpiperazine (3.7 g) as a solid; NMR Spectrum: (CDCl$_3$) 1.05 (d, 6H), 2.75 (m, 1H), 2.8 (m, 4H), 3.45 (m, 2H), 3.55 (m, 2H).

[2] The reactants were 4-(5-chloro-2,3-methylenedioxypyrid-4-ylamino)-7-(3-chloropropoxy)-6-methoxyquinazoline and 1-(2,2,2-trifluoroethyl)piperazine. The reaction mixture was heated to 120° C. for 3 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The material so obtained was dissolved in methylene chloride and an ion exchange resin (diethylaminopolystyrene resin, 4 equivalents) was added and the mixture was stirred for 30 minutes. The mixture was filtered and the filtrate was evaporated. The resultant residue was triturated under pentane to give the required product in 72% yield which gave the following characterising data; NMR Spectrum: (CDCl$_3$) 2.1 (m, 2H), 2.5 (m, 6H), 2.7 (m, 4H), 2.95 (q, 2H), 4.05 (s, 3H), 4.25 (t, 2H), 6.1 (s, 2H), 7.1 (br s, 1H), 7.3 (s, 1H), 7.75 (s, 1H), 8.35 (br s, 1H); Mass Spectrum: M+H$^+$ 555 and 557; Elemental Analysis: Found C, 51.8; H, 5.0; N, 14.8; C$_{24}$H$_{26}$ClF$_3$N$_6$O$_4$ requires C, 51.9; H, 4.7; N, 15.1%.

The 1-(2,2,2-trifluoroethyl)piperazine used as a starting material was prepared as follows:—

2,2,2-Trifluoroethyl trifluoromethanesulphonate (8.2 g) was added to a stirred mixture of 1-tert-butoxycarbonylpiperazine (6 g), potassium carbonate (5.77 g) and acetonitrile (30 ml) and the resultant mixture was stirred at ambient temperature for 16 hours. The mixture was filtered and the filtrate was evaporated. The residue was purified by column chromatography on silica using increasingly polar mixtures of petroleum ether (b.p 40-60° C.) and ethyl acetate as eluent. There was thus obtained tert-butyl 4-(2,2,2-trifluoroethylpiperazine-1-carboxylate as a solid (8.1 g); NMR Spectrum: (CDCl$_3$) 1.45 (s, 9H), 2.6 (m, 4H), 2.95 (q, 2H), 3.4 (m, 4H).

Hydrogen chloride gas was bubbled through a solution of tert-butyl 4-(2,2,2-trifluoroethylpiperazine-1-carboxylate (8 g) in ethyl acetate (50 ml) during 1.5 hours. A precipitate formed as carbon dioxide gas was evolved. The precipitate was collected by filtration, washed with ethyl acetate and dried under vacuum. There was thus obtained 1-(2,2,2-trifluoroethyl)piperazine hydrochloride (7 g); NMR Spectrum: (DMSOd$_6$ and CF$_3$CO$_2$D) 2.85 (m, 4H), 3.1 (m, 4H), 3.35 (q, 2H).

The material so obtained was suspended in methylene chloride and a saturated methanolic ammonia solution (20 ml) was added. The resultant mixture was stirred at ambient temperature for 20 minutes. The mixture was filtered and the filtrate was evaporated at ambient temperature under vacuum. There was thus obtained 1-(2,2,2-trifluoroethyl)piperazine which was used without any additional purification.

[3] The reactants were 7-(2-chloroethoxy)-4-(5-chloro-2,3-methylenedioxypyrid-4-ylamino)-6-methoxyquinazoline and 1-prop-2-ynylpiperazine. The required product was obtained in 52% yield and gave the following characterising data; NMR Spectrum: (DMSOd$_6$ and CF$_3$CO$_2$D) 3.3 (br s, 4H), 3.6 (br s, 4H), 3.75 (br s, 3H), 3.95 (s, 2H), 4.05 (s, 3H), 4.65 (t, 2H), 6.3 (s, 2H), 7.5 (s, 1H), 7.9 (s, 1H), 8.2 (s, 1H), 9.0 (s, 1H); Mass Spectrum: M+H$^+$ 497 and 499; Elemental Analysis: Found C, 56.3; H, 5.4; N, 16.2; C$_{24}$H$_{25}$ClN$_6$O$_4$ 0.7H$_2$O requires C, 56.6; H, 5.2; N, 16.5%.

[4] The reactants were 7-(2-chloroethoxy) 4-(5-chloro-2,3-methylenedioxypyrid-4-ylamino)-5-tetrahydropyran-4-yloxyquinazoline and 1-acetylpiperazine. The reaction mixture was heated to 80° C. for 3 hours and then to 110° C. for 5 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 7.5. The solution was extracted with methylene chloride and the organic phase was dried over magnesium sulphate and evaporated. The resultant residue was triturated under diethyl ether to give the required product in 45% yield which gave the following characterising data; NMR Spectrum: (CDCl$_3$) 2.0 (m, 2H), 2.1 (s, 3H), 2.3 (m, 2H), 2.6 (m, 4H), 2.95 (m, 2H), 3.55 (m, 2H), 3.65 (m, 4H), 4.1 (m, 2H), 4.3 (m, 2H), 4.8 (m, 1H), 6.2 (s, 2H), 6.6 (s, 1H), 6.9 (s, 1H), 7.8 (s, 1H), 8.65 (s, 1H), 9.5 (s, 1H); Mass Spectrum: M+H$^+$ 571 and 573; Elemental Analysis: Found C, 55.3; H, 5.4; N, 13.9; C$_{27}$H$_{31}$ClN$_6$O$_6$ 1H$_2$O requires C, 55.1; H, 5.7; N, 14.3.

[5] The reactants were 7-(2-chloroethoxy)-4-(5-chloro-2,3-methylenedioxypyrid-4-ylamino)-5-tetrahydropyran-4-yloxyquinazoline and (3RS,4SR)-3,4-methylenedioxypyrrolidine. The reaction mixture was heated to 80° C. for 3 hours and then to 110° C. for 5 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 7.5. The solution was extracted with methylene chloride and the organic phase was dried over magnesium sulphate and evaporated. The resultant residue was triturated under diethyl ether to give the required product in 69% yield which gave the following characterising data; NMR Spectrum: (CDCl$_3$) 2.0 (m, 2H), 2.3 (m, 2H), 2.4 (m, 2H), 2.3 (t, 2H), 3.3 (d, 2H), 3.55 (m, 2H), 4.1 (m, 2H), 4.3 (t, 2H), 4.65 (m, 2H), 4.8 (m, 1H), 4.9 (s, 1H), 5.2 (s, 1H), 6.2 (s, 2H), 6.6 (s, 1H), 6.9 (s, 1H), 7.8 (s, 1H), 8.65 (s, 1H), 9.5 (s, 1H); Mass Spectrum: M+H$^+$ 558 and 560; Elemental Analysis: Found C, 56.5; H, 5.3; N, 12.5; C$_{26}$H$_{28}$ClN$_5$O$_7$ 0.2Et$_2$O requires C, 56.2; H, 5.3; N, 12.2%.

The (3RS,4SR)-3,4-methylenedioxypyrrolidine used as a starting material was prepared as follows:—

A solution of di-tert-butyl dicarbonate (Boc$_2$O, 78.95 g) in ethyl acetate (125 ml) was added dropwise to a stirred mixture of 3-pyrroline (25 g; 65% pure containing pyrrolidine) and ethyl acetate (125 ml) which had been cooled to 0° C. The reaction temperature was maintained at 5-10° C. during the addition. The resultant reaction mixture was allowed to warm to ambient temperature overnight. The reaction mixture was washed successively with water, 0.1N aqueous hydrochloric acid solution, water, a saturated aqueous sodium bicarbonate solution and brine, dried over magnesium sulphate and evaporated. There was thus obtained, as a colorless oil (62 g), a 2:1 mixture of tert-butyl 3-pyrroline-1-carboxylate, NMR: (CDCl$_3$) 1.45 (s, 9H), 4.1 (d, 4H), 6.75 (m, 2H), and tert-butyl pyrrolidine-1-carboxylate, NMR: (CDCl$_3$) 1.5 (s, 9H), 1.8 (br s, 4H), 3.3 (br s, 4H).

A solution of the mixture of materials so obtained in acetone (500 ml) was added dropwise to a mixture of N-methylmorpholine-N-oxide (28.45 g), osmium tetroxide (1 g) and water (500 ml) whilst keeping the reaction temperature below 25° C. The reaction mixture was then stirred at ambient temperature for 5 hours. The solvent was evaporated and the residue was partitioned between ethyl acetate and water. The organic phase was washed with brine, dried over magnesium sulphate and evaporated. The residue was purified by column chromatography on silica using increasingly polar mixtures of petroleum ether (b.p. 40-60° C.) and ethyl acetate as eluent and by further column chromatography on silica using increasingly polar mixtures of methylene chloride and methanol. There was thus obtained tert-butyl (3RS, 4SR)-3,4-dihydroxypyrrolidine-1-carboxylate as an oil (34.6 g); NMR Spectrum: (CDCl$_3$) 1.45 (s, 9H), 2.65 (m, 2H), 3.35 (m, 2H), 3.6 (m, 2H), 4.25 (m, 2H).

A solution of tert-butyl (3RS,4SR)-3,4-dihydroxypyrrolidine-1-carboxylate (34.6 g) in DMF (400 ml) was cooled to 0-5° C. and sodium hydride (60% dispersion in mineral oil, 0.375 mol) was added portionwise. The reaction mixture was stirred at 5° C. for 1 hour. Dibromomethane (15.6 ml) was added and the reaction mixture was stirred at 5° C. for 30 minutes. The reaction mixture was allowed to warm to ambient temperature and was stirred for 16 hours. The DMF was evaporated and the residue was partitioned between ethyl acetate and water. The organic phase was washed with water and with brine, dried over magnesium sulphate and evaporated. The residue was purified by column chromatography on silica using increasingly polar mixtures of petroleum ether (b.p. 40-60° C.) and ethyl acetate as eluent. There was thus obtained tert-butyl (3RS,4SR)-3,4-methylenedioxypyrrolidine-1-carboxylate as a colourless oil (19.77 g); NMR Spectrum: (CDCl$_3$) 1.45 (s, 9H), 3.35 (m, 2H), 3.75 (br s, 2H), 4.65 (m, 2H), 4.9 (s, 1H), 5.1 (s, 1H).

A cooled 5M solution of hydrogen chloride in isopropanol (150 ml) was added to a solution of tert-butyl (3RS,4SR)-3,4-methylenedioxypyrrolidine-1-carboxylate (19.7 g) in methylene chloride (500 ml) that was cooled in an ice bath. The reaction mixture was allowed to warm to ambient temperature and was stirred for 4 hours. The solvent was evaporated and the residue was triturated under diethyl ether. The precipitate was collected by filtration, washed with diethyl ether and dried. There was thus obtained (3RS,4SR)-3,4-methylenedioxypyrrolidine hydrochloride as a beige solid (13.18 g); NMR Spectrum: (DMSOd$_6$) 3.15 (m, 2H), 3.35 (m, 2H), 4.65 (s, 1H), 4.8 (m, 2H), 5.1 (s, 1H).

The material so obtained was suspended in diethyl ether and a saturated methanolic ammonia solution was added. The resultant mixture was stirred at ambient temperature for 10 minutes. The mixture was filtered and the solvent was evaporated at ambient temperature under vacuum. There was thus obtained (3RS,4SR)-3,4-methylenedioxypyrrolidine which was used without any additional purification.

[6] The reactants were 7-(2-chloroethoxy)-4-(5-chloro-2,3-methylenedioxypyrid-4-ylamino)-5-isopropoxyquinazoline and 1-acetylpiperazine. The reaction mixture was heated to 85° C. for 8 hours. The reaction product was purified by column chromatography on silica using increasingly polar mixtures of methylene chloride and methanol as eluent. The product was obtained in 89% yield and gave the following characterising data; m.p. 208-210° C.; NMR Spectrum: (CDCl$_3$) 1.55 (d, 6H), 2.1 (s, 3H), 2.6 (m, 4H), 2.9 (t, 2H), 3.5 (t, 2H), 3.7 (t, 2H), 4.25 (t, 2H), 4.85 (m, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 529 and 531; Elemental Analysis: Found C, 57.0; H, 5.7; N, 15.7; C$_{25}$H$_{29}$ClN$_6$O$_5$ requires C, 56.8; H, 5.5; N, 15.9%.

[7] The reactants were 7-(2-chloroethoxy)-4-(5-chloro-2,3-methylenedioxypyrid-4-ylamino)-5-isopropoxyquinazoline and (3RS,4SR)-3,4-methylenedioxypyrrolidine. The reaction mixture was heated to 95° C. for 3 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 7. The solution was extracted with methylene chloride and the organic phase was dried over magnesium sulphate and evaporated. The resultant residue was triturated under diethyl ether to give the required product in 64% yield which gave the following characterising data; NMR Spectrum: (CDCl$_3$) 1.55 (d, 6H), 2.35 (m, 2H), 2.9 (t, 2H), 3.25 (d, 2H), 4.25 (t, 2H), 4.6 (m, 2H), 4.85 (m, 1H), 4.9 (s, 1H), 5.15 (s, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 516 and 518; Elemental Analysis: Found C, 54.7; H, 5.2; N, 13.2; C$_{24}$H$_{26}$ClN$_5$O$_6$ 0.5H$_2$O requires C, 54.9; H, 5.2; N, 13.3%.

[8] The reactants were 4-(5-chloro-2,3-methylenedioxypyrid-4-ylamino) 6-(2-chloroethoxy)7-methoxyquinazoline (the preparation of which is described in Example 7 hereinafter) and morpholine. The reaction mixture was heated to 120° C. for 16 hours. The required product was obtained in 69% yield and gave the following characterising data; NMR Spectrum: (CDCl$_3$ and CD$_3$CO$_2$D) 3.3 (m, 4H), 3.5 (t, 2H), 3.95 (m, 4H), 4.05 (s, 3H), 4.6 (t, 2H), 6.15 (s, 2H), 7.6 (s, 1H), 7.8 (s, 2H), 8.6 (s, 1H); Mass Spectrum: M+H$^+$ 460 and 462; Elemental Analysis: Found C, 53.45; H, 4.8; N, 14.5; C$_{21}$H$_{22}$ClN$_5$O$_5$ 0.55H$_2$O requires C, 53.7; H, 5.0; N, 14.9%.

[9] The reactants were 4-(5-chloro-2,3-methylenedioxypyrid-4-ylamino)-6-(2-chloroethoxy)-7-methoxyquinazoline and 1-methylpiperazine. The reaction mixture was heated to 120° C. for 16 hours. The reaction product was purified by column chromatography on a Waters X-Terra silica column (C18 reversed-phase, 5 microns, 19 mm diameter, 100 mm length; Waters Inc., Milford, Mass. 01757, USA) and eluted with decreasingly polar mixtures of an ammonium carbonate buffer (2 g/L in water) and acetonitrile. Appropriate fractions were collected, the organic solvent was evaporated and the resultant mixture was partitioned between ethyl acetate and a saturated aqueous sodium bicarbonate solution. The organic phase was dried over magnesium sulphate and evaporated. There was thus obtained the required product in 29% yield which gave the following characterising data; NMR Spectrum: (CDCl$_3$ and CD$_3$CO$_2$D) 2.7 (s, 3H), 3.25-3.35 (br m, 10H), 4.05 (s, 3H), 4.45 (t, 2H), 6.15 (s, 2H), 7.55 (s, 1H), 7.7 (s, 1H), 7.8 (s, 1H), 8.65 (s, 1H); Mass Spectrum: M+H$^+$ 473 and 475; Elemental Analysis: Found C, 54.9; H, 5.3; N, 17.1; C$_{22}$H$_{25}$ClN$_6$O$_4$ 0.4H$_2$O requires C, 55.0; H, 5.4; N, 17.5%.

[10] The reactants were 4-(5-chloro-2,3-methylenedioxypyrid-4-ylamino)-6-(2-chloroethoxy)-7-methoxyquinazoline and pyrrolidine. The reaction mixture was heated to 120° C. for 16 hours. The required product was obtained in 41% yield and gave the following characterising data; NMR Spectrum: (CDCl$_3$ and CD$_3$CO$_2$D) 2.15 (m, 4H), 3.3-3.6 (br s, 4H), 3.7 (t, 2H), 4.05 (s, 3H), 4.65 (t, 2H), 6.15 (s, 2H), 7.65 (s, 1H), 7.8 (s, 1H), 7.9 (s, 1H), 8.65 (s, 1H); Mass Spectrum: M+H$^+$ 444 and 446; Elemental Analysis: Found C, 55.0; H, 5.0; N, 14.9; $C_{21}H_{22}ClN_5O_4$ 0.7H$_2$O requires C, 55.25; H, 5.2; N, 15.3%.

[11] The reactants were 4-(5-chloro-2,3-methylenedioxypyrid-4-ylamino)-6-(2-chloroethoxy)-7-methoxyquinazoline and 1-acetylpiperazine. The reaction mixture was heated to 120° C. for 16 hours. The required product was obtained in 51% yield and gave the following characterising data; NMR Spectrum: (CDCl$_3$ and CD$_3$CO$_2$D) 2.15 (s, 3H), 3.1 (m, 2H), 3.2 (m, 2H), 3.4 (t, 2H), 3.75 (m, 2H), 3.85 (m, 2H), 4.0 (s, 3H), 4.55 (t, 2H), 6.15 (s, 2H), 7.6 (s, 1H), 7.7 (s, 1H), 7.8 (s, 1H), 8.6 (s, 1H); Mass Spectrum: M+H$^+$ 501 and 503.

[12] The reactants were 4-(5-chloro-2,3-methylenedioxypyrid-4-ylamino)-6-(2-chloroethoxy)-7-methoxyquinazoline and (3RS,4SR)-3,4-methylenedioxypyrrolidine. The reaction mixture was heated to 120° C. for 16 hours. The required product was obtained in 73% yield and gave the following characterising data; NMR Spectrum: (CDCl$_3$ and CD$_3$CO$_2$D) 2.95 (m, 2H), 3.45 (t, 2H), 3.65 (d, 2H), 4.05 (s, 3H), 4.55 (t, 2H), 4.8 (m, 3H), 5.2 (s, 1H), 6.15 (s, 2H), 7.6 (s, 1H), 7.75 (s, 1H), 7.8 (s, 1H), 8.65 (s, 1H); Mass Spectrum: M+H$^+$ 488 and 490.

[13] The reactants were 4-(5-chloro-2,3-methylenedioxypyrid-4-ylamino)-6-(3-chloropropoxy)-7-methoxyquinazoline (the preparation of which is described in Example 8 hereinafter) and pyrrolidine. The reaction mixture was heated to 120° C. for 16 hours. The required product was obtained in 50% yield and gave the following characterising data; NMR Spectrum: (CDCl$_3$ and CD$_3$CO$_2$D) 2.1 (m, 4H), 2.4 (m, 2H), 3.0-3.8 (br s, 4H), 3.4 (t, 2H), 4.05 (s, 3H), 4.35 (t, 3H), 6.1 (s, 2H), 7.6 (s, 1H), 7.75 (s, 1H), 7.8 (s, 1H), 8.65 (s, 1H); Mass Spectrum: M+H$^+$ 458 and 460; Elemental Analysis: Found C, 57.3; H, 5.4; N, 14.5; $C_{22}H_{24}ClN_5O_4$ 0.15H$_2$O requires C, 57.4; H, 5.3; N, 15.2%.

[14] The reactants were 4-(5-chloro-2,3-methylenedioxypyrid-4-ylamino)-6-(3-chloropropoxy)-7-methoxyquinazoline and morpholine. The reaction mixture was heated to 120° C. for 16 hours. The required product was obtained in 72% yield and gave the following characterising data; NMR Spectrum: (CDCl$_3$) 2.1 (m, 2H), 2.5 (m, 4H), 2.6 (t, 2H), 3.7 (m, 4H), 4.05 (s, 3H), 4.25 (t, 2H), 6.1 (s, 2H), 7.05 (s, 1H), 7.15 (s, 1H), 7.3 (s, 1H), 7.75 (s, 1H), 8.7 (s, 1H); Mass Spectrum: M+H$^+$ 474 and 476.

[15] The reactants were 4-(5-chloro-2,3-methylenedioxypyrid-4-ylamino)-6-(3-chloropropoxy)-7-methoxyquinazoline and 1-acetylpiperazine. The reaction mixture was heated to 120° C. for 16 hours. The required product was obtained in 39% yield and gave the following characterising data; NMR Spectrum: (CDCl$_3$ and CD$_3$CO$_2$D) 2.15 (s, 3H), 2.35 (m, 2H), 3.15-3.3 (m, 6H), 3.8 (m, 2H), 3.9 (m, 2H), 4.0 (s, 3H), 4.3 (t, 2H), 6.15 (s, 2H), 7.6 (s, 1H), 7.65 (s, 1H), 7.8 (s, 1H), 8.65 (s, 1H); Mass Spectrum: M+H$^+$ 515 and 517.

[16] The reactants were 4-(5-chloro-2,3-methylenedioxypyrid-4-ylamino)-6-(3-chloropropoxy)-7-methoxyquinazoline and 1-acetylpiperazine. The reaction mixture was heated to 120° C. for 16 hours. The required product was obtained in 27% yield and gave the following characterising data; NMR Spectrum: (CDCl$_3$ and CD$_3$CO$_2$D) 2.3 (m, 2H), 2.7 (s, 3H), 3.3 (t, 2H), 3.4 (m, 4H), 3.5 (m, 4H), 4.0 (s, 3H), 4.3 (t, 2H), 6.15 (s, 2H), 7.6 (s, 1H), 7.65 (s, 1H), 7.8 (s, 1H), 8.65 (s, 1H); Mass Spectrum: M+H$^+$ 487 and 489.

[17] The reactants were 4-(5-chloro-2,3-methylenedioxypyrid-4-ylamino)-6-(3-chloropropoxy)-7-methoxyquinazoline and (3RS,4SR)-3,4-methylenedioxypyrrolidine. The reaction mixture was heated to 95° C. for 3 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 7. The solution was extracted with methylene chloride and the organic phase was dried over magnesium sulphate and evaporated. The resultant residue was triturated under diethyl ether to give the required product in 57% yield which gave the following characterising data; NMR Spectrum: (CDCl$_3$ and CD$_3$CO$_2$D) 2.3 (m, 2H), 3.3 (m, 2H), 3.4 (t, 2H), 3.6 (d, 2H), 4.0 (s, 3H), 4.3 (t, 2H), 4.8 (m, 3H), 5.2 (s, 1H), 6.15 (s, 2H), 7.55 (s, 1H), 7.6 (s, 1H), 7.8 (s, 1H), 8.6 (s, 1H); Mass Spectrum: M+H$^+$ 502 and 504.

[18] The reactants were 4-(5-chloro-2,3-methylenedioxypyrid-4-ylamino)-7-(2-chloroethoxy)-5-tetrahydropyran-4-yloxyquinazoline and 1-prop-2-ynylpiperazine. The reaction mixture was heated to 80° C. for 3 hours and then to 110° C. for 5 hours. The reaction product was purified by column chromatography on a Waters X-Terra silica column (C18 reversed-phase, 5 microns, 19 mm diameter, 100 mm length) and eluted with decreasingly polar mixtures of an ammonium carbonate buffer (2 g/L in water) and acetonitrile. Appropriate fractions were collected, the organic solvent was evaporated and the resultant mixture was partitioned between ethyl acetate and a saturated aqueous sodium bicarbonate solution. The organic phase was dried over magnesium sulphate and evaporated. There was thus obtained the required product in 54% yield which gave the following characterising data; NMR Spectrum: (DMSOd$_6$ and CD$_3$CO$_2$D) 1.85 (m, 2H), 2.15 (m, 2H), 2.5-3.0 (m, 10H), 3.15 (s, 1H), 3.3 (s, 2H), 3.55 (t, 2H), 3.9 (m, 2H), 4.3 (m, 2H), 5.05 (m, 1H), 6.2 (s, 2H), 6.9 (s, 2H), 7.8 (s, 1H), 8.5 (s, 1H); Mass Spectrum: M+H$^+$ 567 and 569; Elemental Analysis: Found C, 55.9; H, 5.6; N, 14.0; $C_{28}H_{31}ClN_6O_5$ 2H$_2$O requires C, 55.8; H, 5.85; N, 13.9%.

[19] Using the detailed conditions described in Note [18] immediately above, 4-(5-chloro-2,3-methylenedioxypyrid-4-ylamino)-7-(2-chloroethoxy)-5-tetrahydropyran-4-yloxyquinazoline was reacted with morpholine to give the required product in 48% yield which gave the following characterising data; NMR Spectrum: (DMSOd$_6$ and CD$_3$CO$_2$D) 1.8 (m, 2H), 2.15 (m, 2H), 2.55 (m, 4H), 2.8 (m, 2H), 3.5 (m, 2H), 3.6 (m, 4H), 3.9 (m, 2H), 4.3 (t, 2H), 5.1 (m, 1H), 6.2 (s, 2H), 6.9 (m, 2H), 7.8 (s, 1H), 8.45 (s, 1H); Mass Spectrum: M+H$^+$ 530 and 532; Elemental Analysis: Found C, 51.8; H, 5.8; N, 12.1; $C_{25}H_{28}ClN_5O_6$ 2.5H$_2$O requires C, 52.2; H, 5.8; N, 12.2%.

[20] The reactants were 4-(5-chloro-2,3-methylenedioxypyrid-4-ylamino)-7-(3-chloropropoxy)-5-tetrahydropyran-4-yloxyquinazoline (described in Example 9 hereinafter) and morpholine. The required product was obtained in 30% yield and gave the following characterising data; NMR Spectrum: (CDCl$_3$ and CF$_3$CO$_2$D) 2.05 (m, 2H), 2.35 (m, 4H), 3.15 (m, 2H), 3.45 (m, 2H), 3.75 (m, 4H), 3.9 (m, 2H), 4.2 (m, 6H), 5.0 (m, 1H), 6.3 (s, 2H), 6.85 (s, 1H), 7.0 (s, 1H), 7.9 (s; 1H), 8.7 (s, 1H); Mass Spectrum: M+H$^+$ 544 and 546.

[21] The reactants were 4-(5-chloro-2,3-methylenedioxypyrid-4-amino)-7-(3-chloropropoxy)-5-tetrahydropyran-4-yloxyquinazoline and 1-prop-2-ynylpiperazine. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 9. The solution was extracted with methylene chloride and the organic phase was dried over magnesium sulphate and evaporated. The resultant residue was triturated under pentane to give the required product in 48% yield which gave the following characterising data; NMR Spectrum: (DMSOd$_6$ and CD$_3$CO$_2$D) 1.85 (m, 2H), 2.0 (m, 2H), 2.15 (m, 2H), 2.5-2.8 (br m, 10H), 3.15 (s, 1H), 3.3 (s, 2H), 3.55 (t, 2H), 3.9 (m, 2H), 4.2 (t, 2H), 5.05 (m, 1H), 6.2 (s, 2H), 6.85 (s, 1H), 6.9 (s, 1H), 7.8 (s, 1H), 8.45 (s, 1H); Mass Spectrum: M+H$^+$ 581 and 583.

[22] The reactants were 7-(2-chloroethoxy)-4-(5-chloro-2,3-methylenedioxypyrid-4-ylamino)-5-isopropoxyquinazoline and piperazine. The required product was obtained in 30% yield and gave the following characterising data; NMR Spectrum: (CDCl$_3$) 1.55 (d, 6H), 2.6 (m, 4H), 2.85 (t, 2H), 2.95 (m, 4H), 4.25 (t, 2H), 4.85 (m, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 487 and 489; Elemental Analysis: Found C, 55.4; H, 5.5; N, 16.4; C$_{23}$H$_{27}$ClN$_6$O$_4$ 0.1Et$_2$O 0.6H$_2$O requires C, 55.65; H, 5.8; N, 16.6%.

[23] The reactants were 7-(2-chloroethoxy)-4-(5-chloro-2,3-methylenedioxypyrid-4-ylamino)-5-isopropoxyquinazoline and 1-(2-hydroxyethyl)piperazine. The reaction mixture was heated to 85° C. for 8 hours. The reaction product was purified by column chromatography on silica using increasingly polar mixtures of methylene chloride and methanol as eluent. The material so obtained was triturated under diethyl ether to give the required product in 67% yield which gave the following characterising data; NMR Spectrum: (CDCl$_3$) 1.5 (d, 6H), 2.5-2.7 (br m, 12H), 3.65 (t, 2H), 4.25 (t, 2H), 4.8 (m, 1H), 6.15 (s, 2H), 6.6 (s, 1H), 6.85 (s, 1H), 7.25 (s, 1H), 7.75 (s, 1H), 8.6 (s, 1H), 9.6 (s, 1H); Mass Spectrum: M+H$^+$ 531 and 533; Elemental Analysis: Found C, 55.4; H, 6.05; N, 15.2; C$_{25}$H$_{31}$ClN$_6$O$_5$ 0.1Et$_2$O 0.5H$_2$O requires C, 55.7; H, 6.1; N, 15.35%.

[24] The reactants were 7-(2-chloroethoxy)-4-(5-chloro-2,3-methylenedioxypyrid-4-ylamino)-5-isopropoxyquinazoline and pyrrolidine. The reaction mixture was heated to 80° C. for 4 hours. The reaction product was purified by column chromatography on a C18 reversed phase silica column (Waters Symmetry column, 5 microns silica, 19 mm diameter, 100 mm length) using a decreasingly polar mixture of water and acetonitrile (containing 1% acetic acid) as eluent. The organic solvents were evaporated and the pH of the aqueous phase was adjusted to 9. The solution was extracted with methylene chloride and the organic phase was dried over magnesium sulphate and evaporated. The resultant residue was triturated under pentane to give the required product in 62% yield which gave the following characterising data; NMR Spectrum: (CDCl$_3$) 1.55 (d, 6H), 1.85 (m, 4H), 2.6 (m, 4H), 2.95 (t, 2H), 4.25 (t, 2H), 4.85 (m, 1H), 6.15 (s, 2H), 6.6 (s, 1H), 6.85 (s, 1H), 7.75 (s, 1H), 8.6 (s, 1H), 9.6 (s, 1H); Mass Spectrum: M+H$^+$ 472 and 474; Elemental Analysis: Found C, 58.3; H, 5.4; N, 14.7; C$_{23}$H$_{26}$ClN$_5$O$_4$ requires C, 58.5; H, 5.55; N, 14.8%.

[25] Using the detailed conditions described in Note [24] immediately above, 4-(5-chloro-2,3-methylenedioxypyrid-4-ylamino)-7-(2-chloroethoxy)-5-tetrahydropyran-4-yloxyquinazoline was reacted with piperidine to give the required product in 52% yield which gave the following characterising data; NMR Spectrum: (CDCl$_3$) 1.45 (m, 2H), 1.55 (d, 6H), 1.65 (m, 4H), 2.5 (m, 4H), 2.85 (t, 2H), 4.25 (t, 2H), 4.85 (m, 1H), 6.15 (s, 2H), 6.6 (s, 1H), 6.85 (s, 1H), 7.75 (s, 1H), 8.6 (s, 1H), 9.6 (s, 1H); Mass Spectrum: M+H$^+$ 486 and 488; Elemental Analysis: Found C, 59.3; H, 5.9; N, 14.4; C$_{24}$H$_{28}$ClN$_5$O$_4$ requires C, 59.3; H, 5.8; N, 14.4%.

[26] Using the detailed conditions described in Note [24] immediately above, 4-(5-chloro-2,3-methylenedioxypyrid-4-ylamino)-7-(2-chloroethoxy)-5-tetrahydropyran-4-yloxyquinazoline was reacted with morpholine to give the required product in 57% yield which gave the following characterising data; NMR Spectrum: (CDCl$_3$) 1.55 (d, 6H), 2.6 (m, 4H), 2.85 (t, 2H), 3.75 (m, 4H), 4.25 (t, 2H), 4.85 (m, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 488 and 490; Elemental Analysis: Found C, 56.6; H, 5.4; N, 14.2; C$_{23}$H$_{26}$ClN$_5$O$_5$ requires C, 56.6; H, 5.4; N, 14.35%.

[27] Using the detailed conditions described in Note [24] immediately above, 4-(5-chloro-2,3-methylenedioxypyrid-4-ylamino)-7-(2-chloroethoxy)-5-tetrahydropyran-4-yloxyquinazoline was reacted with 1-prop-2-ynylpiperazine to give the required product in 41% yield which gave the following characterising data; NMR Spectrum: (CDCl$_3$) 1.55 (d, 6H), 2.25 (s, 1H), 2.65 (br m, 8H), 2.9 (t, 2H), 3.3 (s, 2H), 4.25 (t, 2H), 4.85 (m, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 525 and 527; Elemental Analysis: Found C, 59.3; H, 5.4; N, 15.85; C$_{26}$H$_{29}$ClN$_6$O$_4$ requires C, 59.5; H, 5.6; N, 16.0%.

[28] The reactants were 7-(2-chloroethoxy)-4-(5-chloro-2,3-methylenedioxypyrid-4-ylamino)-5-isopropoxyquinazoline and (3RS,4SR)-3,4-dimethoxypyrrolidine. The required product was obtained in 78% yield and gave the following characterising data; NMR Spectrum: (DMSOd$_6$ and CD$_3$CO$_2$D) 1.45 (d, 6H), 2.7 (m, 2H), 3.0 (m, 2H), 3.15 (m, 2H), 3.3 (s, 6H), 3.75 (m, 2H), 4.25 (t, 2H), 5.5 (m, 1H), 6.2 (s, 2H), 6.8 (s, 1H), 6.85 (s, 1H), 7.8 (s, 1H), 8.45 (s, 1H); Mass Spectrum: M+H$^+$ 532 and 534; Elemental Analysis: Found C, 56.0; H, 5.6; N, 12.85; C$_{25}$H$_{30}$ClN$_5$O$_6$ 0.3H$_2$O requires C, 56.25; H, 5.7; N, 13.1%.

The (3RS,4SR)-3,4-dimethoxypyrrolidine used as a starting material was obtained as follows:—

A solution of tert-butyl (3RS,4SR)-3,4-dihydroxypyrrolidine-1-carboxylate (1 g) in DMF (20 ml) was cooled to 0-5° C. and sodium hydride (60% dispersion in mineral oil, 0.433 g) was added portionwise. The reaction mixture was stirred at 5° C. for 1 hour. Methyl iodide (0.675 ml) was added and the reaction mixture was allowed to warm to ambient temperature and was stirred for 16 hours. The DMF was evaporated and the residue was partitioned between diethyl ether and water. The organic phase was washed with water and with brine, dried over magnesium sulphate and evaporated. The residue was purified by column chromatography on silica using increasingly polar mixtures of petroleum ether (b.p. 40-60° C.) and ethyl acetate as eluent. There was thus obtained tert-butyl (3RS,4SR)-3,4-dimethoxypyrrolidine-1-carboxylate as an oil (1.06 g); NMR Spectrum: (CDCl$_3$) 1.45 (s, 9H), 3.35 (m, 1H), 3.45 (s, 6H), 3.5 (m, 2H), 3.55 (m, 1H), 3.85 (m, 2H).

A cooled 5M solution of hydrogen chloride in isopropanol (3 ml) was added to a solution of tert-butyl (3RS,4SR)-3,4-dimethoxypyrrolidine-1-carboxylate (1 g) in methylene chloride (25 ml) that was cooled in an ice bath. The reaction mixture was allowed to warm to ambient temperature and was stirred for 16 hours. The solvent was evaporated. There was thus obtained (3RS,4SR)-3,4-dimethoxypyrrolidine hydrochloride as an oil (0.72 g); NMR Spectrum: (DMSOd$_6$) 3.1 (m, 2H), 3.25 (m, 2H), 3.35 (s, 6H), 4.0 (m, 2H), 9.3 (br s, 1H), 9.5 (br s, 1H).

The material so obtained was dissolved in methylene chloride and a 7M methanolic ammonia solution (0.2 ml) was added. The resultant mixture was stirred at ambient temperature for 5 minutes. The mixture was filtered and the solvent was evaporated at ambient temperature under vacuum. There was thus obtained (3RS,4SR)-3,4-dimethoxypyrrolidine which was used without any additional purification.

[29] Using the detailed conditions described in Note [24] immediately above except that the product was triturated under diethyl ether rather than under pentane, 4-(5-chloro-2,3-methylenedioxypyrid-4-ylamino)-7-(2-chloroethoxy)-5-tetrahydropyran-4-yloxyquinazoline was reacted with (3RS,4SR)-3,4-ethylidenedioxypyrrolidine to give the required product in 67% yield which gave the following characterising data; NMR Spectrum: (CDCl$_3$) 1.45 (d, 3H), 1.55 (d, 6H), 2.3 (d, 2H), 2.95 (m, 2H), 3.25 (d, 2H), 4.25 (t, 2H), 4.55 (m, 2H), 4.8 (m, 1H), 5.0 (m, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 530 and 532; Elemental Analysis: Found C, 56.7; H, 5.5; N, 12.9; C$_{25}$H$_{28}$ClN$_5$O$_6$ 0.1Et$_2$O requires C, 56.8; H, 5.4; N, 13.0%.

The (3RS,4SR)-3,4-ethylidenedioxypyrrolidine used as a starting material was obtained as follows:—

A solution of tert-butyl (3RS,4SR)-3,4-dihydroxypyrrolidine-1-carboxylate (0.5 g) in methylene chloride (15 ml) was cooled to 0-5° C. and acetaldehyde dimethylacetal (0.782 ml) and 4-toluenesulphonic acid (0.025 g) were added in turn. The reaction mixture was stirred at ambient temperature for 2 hours. The resultant mixture was evaporated and the residue was purified by column chromatography on silica using increasingly polar mixtures of petroleum ether (b.p. 40-60° C.) and ethyl acetate as eluent. There was thus obtained tert-butyl (3RS,4SR)-3,4-ethylidenedioxypyrrolidine-1-carboxylate as an oil (0.484 g); NMR Spectrum: (CDCl$_3$) 1.4 (d, 3H), 1.45 (s, 9H), 3.3 (m, 2H), 3.8 (m, 2H), 4.6 (m, 2H), 5.0 (q, 1H).

A cooled 5M solution of hydrogen chloride in isopropanol (4 ml) was added to a solution of tert-butyl (3RS,4SR)-3,4-ethylidenedioxypyrrolidine-1-carboxylate (0.475 g) in methylene chloride (25 ml) that was cooled in an ice bath. The reaction mixture was allowed to warm to ambient temperature and was stirred for 2 hours. The solvent was evaporated and the residue was triturated under diethyl ether. The precipitate was collected by filtration, washed with diethyl ether and dried. There was thus obtained (3RS,4SR)-3,4-ethylidenedioxypyrrolidine hydrochloride (0.28 g); NMR Spectrum: (DMSOd$_6$ and CD$_3$CO$_2$D) 1.35 (d, 3H), 3.1 (d, 2H), 3.4 (d, 2H), 4.75 (s, 2H), 4.9 (q, 1H).

The material so obtained was dissolved in methylene chloride and a 7M methanolic ammonia solution (0.2 ml) was added. The resultant mixture was stirred at ambient temperature for 5 minutes. The mixture was filtered and the solvent was evaporated at ambient temperature under vacuum. There was thus obtained (3RS,4SR)-3,4-ethylidenedioxypyrrolidine which was used without any additional purification.

[30] The reactants were 7-(2-chloroethoxy)-4-(5-chloro-2,3-methylenedioxypyrid-4-ylamino)quinazoline and 1-methylpiperazine. The required product was obtained in 74% yield and gave the following characterising data; NMR Spectrum: (CDCl$_3$ and CD$_3$CO$_2$D); Mass Spectrum: M+H$^+$ 501 and 503; Elemental Analysis: Found C, 57.5; H, 6.5; N, 16.0; C$_{24}$H$_{29}$ClN$_6$O$_4$ 0.23H$_2$O requires C, 57.8; H, 6.1; N, 16.2%.

[31] The reactants were 7-(3-chloropropoxy)-4-(5-chloro-2,3-methylenedioxypyrid-4-ylamino)-5-isopropoxyquinazoline (the preparation of which is described in Example 12 hereinafter) and morpholine. The required product was obtained in 39% yield and gave the following characterising data; NMR Spectrum: (CDCl$_3$) 1.55 (d, 6H), 2.05 (m, 2H), 2.45 (m, 4H), 2.55 (t, 2H), 3.7 (m, 4H), 4.15 (t, 2H), 4.85 (m, 1H), 6.15 (s, 2H), 6.5 (s, 1H), 6.85 (s, 1H), 7.75 (s, 1H), 8.6 (s, 1H), 9.6 (s, 1H); Mass Spectrum: M+H$^+$ 502 and 504; Elemental Analysis: Found C, 57.3; H, 5.65; N, 13.6; C$_{24}$H$_{28}$ClN$_5$O$_5$ requires C, 57.4; H, 5.6; N, 13.95%.

[32] The reactants were 7-(3-chloropropoxy)-4-(5-chloro-2,3-methylenedioxypyrid-4-ylamino)quinazoline (the preparation of which is described in Example 13 hereinafter) and morpholine. The required product was obtained in 45% yield and gave the following characterising data; NMR Spectrum: (DMSOd$_6$ and CF$_3$CO$_2$D) 2.3 (m, 2H), 3.15 (m, 2H), 3.35 (m, 2H), 3.5 (m, 2H), 3.7 (m, 2H), 4.05 (m, 2H), 4.35 (m, 2H), 6.3 (s, 2H), 7.35 (s, 1H), 7.6 (d, 1H), 7.9 (s, 1H), 8.7 (d, 1H), 9.05 (s, 1H); Mass Spectrum: M+H$^+$ 444 and 446; Elemental Analysis: Found C, 57.0; H, 5.1; N, 15.7; C$_{21}$H$_{22}$ClN$_5$O$_4$ requires C, 56.8; H, 5.0; N, 15.8%.

[33] The reactants were 7-(3-chloropropoxy)-4-(5-chloro-2,3-methylenedioxypyrid-4-ylamino)quinazoline and 1-acetylpiperazine. The required product was obtained in 34% yield and gave the following characterising data; NMR Spectrum: (DMSOd$_6$ and CF$_3$CO$_2$D) 2.05 (s, 3H), 2.3 (s, 2H), 3.0 (m, 2H), 3.15 (m, 1H), 3.3-3.4 (m, 4H), 3.6 (m, 2H), 4.05 (m, 1H), 4.35 (m, 2H), 4.5 (m, 1H), 6.3 (s, 2H), 7.35 (s, 1H), 7.6 (d, 1H), 7.9 (s, 1H), 8.7 (d, 1H), 9.0 (s, 1H); Mass Spectrum: M+H$^+$ 485 and 487; Elemental Analysis: Found C, 56.9; H, 5.4; N, 16.6; C$_{23}$H$_{25}$ClN$_6$O$_4$ 0.15Et$_2$O requires C, 57.1; H, 5.4; N, 16.9%.

[34] The reactants were 7-(2-chloroethoxy)-4-(2,3-methylenedioxypyrid-4-ylamino)quinazoline (the preparation of which is described in Example 14 hereinafter) and 1-prop-2-ynylpiperazine. After cooling of the reaction mixture and evaporation of the solvent, the residue was triturated under water and the resultant precipitate was isolated, washed with water and diethyl ether and dried. The required product was obtained in 60% yield and gave the following characterising data; NMR Spectrum: (CDCl$_3$) 2.26 (s, 1H), 2.8-2.6 (m, 8H), 2.97 (t, 2H), 3.3 (s, 2H, 4.03 (s, 3H), 4.33 (t, 2H), 6.14 (s, 2H), 6.98 (s, 1H), 7.12 (br s, 1H), 7.30 (s, 1H), 7.73 (d, 1H), 8.08 (d, 1H), 8.76 (s, 1H); Mass Spectrum: M+H$^+$ 463.

[35] The reactants were 7-(3-chloropropoxy)-4-(2,3-methylenedioxypyrid-4-ylamino)quinazoline (the preparation of which is described in Example 15 hereinafter) and 1-prop-2-ynylpiperazine. The required product was obtained in 57% yield and gave the following characterising data; NMR Spectrum: (CDCl$_3$) 2.13 (m, 2H), 2.26 (s, 1H), 2.6 (m, 10H), 3.31 (s, 2H), 4.04 (s, 3H), 4.26 (t, 2H), 6.14 (s, 2H), 6.98 (s, 1H), 7.12 (br s, 1H), 7.31 (s, 1H), 7.72 (d, 1H), 8.08 (d, 1H), 8.76 (s, 1H); Mass Spectrum: M+H$^+$ 477.

EXAMPLE 7

6-(2-chloroethoxy)-4-(5-chloro-2,3-methylenedioxypyrid-4-ylamino)-7-methoxyquinazoline Using an analogous procedure to that described in Example 1, 4-chloro-6-(2-chloroethoxy)-7-methoxyquinazoline was reacted with 4-amino-5-chloro-2,3-methylenedioxypyridine to give the title compound in 59% yield; NMR Spectrum: (CDCl$_3$) 3.95 (t, 2H), 4.05 (s, 3H), 4.4 (t, 2H), 6.1 (s, 2H), 7.05 (s, 1H), 7.2 (s, 1H), 7.35 (s, 1H), 7.75 (s, 1H), 8.75 (s, 1H); Mass Spectrum: M+H$^+$ 409 and 411.

The 4-chloro-6-(2-chloroethoxy)-7-methoxyquinazoline used as a starting material was prepared as follows:—

A mixture of 6-acetoxy-7-methoxy-3,4-dihydroquinazolin-4-one (International Patent Application WO 96/15118, Example 39 thereof; 8 g), thionyl chloride (80 ml) and DMF (0.8 ml) was stirred and heated to 80° C. for 1.5 hours. The mixture was cooled to ambient temperature and the thionyl chloride was evaporated. The material so obtained was suspended in toluene and evaporated to dryness (twice). The resultant residue was diluted with methylene chloride (5 ml) and a 10:1 mixture (290 ml) of methanol and a saturated aqueous ammonium hydroxide solution was added. The resultant mixture was stirred and heated to 80° C. for 5 minutes. The solvent was evaporated and the solid residue was suspended in water. The basicity of the mixture was adjusted to pH7 by the addition of dilute aqueous hydrochloric acid solution. The resultant solid was collected by filtration, washed with water and dried under vacuum over phosphorus pentoxide. There was thus obtained 4-chloro-6-hydroxy-7-methoxyquinazoline (6.08 g) which was used without further purification; NMR Spectrum: (DMSOd$_6$) 4.05 (s, 3H), 7.4 (s, 1H), 7.45 (s, 1H), 8.8 (s, 1H).

Di-tert-butyl azodicarboxylate (1.53 ml) was added portionwise over a few minutes to a stirred mixture of 4-chloro-6-hydroxy-7-methoxyquinazoline (1 g), 2-chloroethanol (0.382 ml), triphenylphosphine (1.74 g) and methylene chloride (30 ml) and the reaction mixture was stirred at ambient temperature for 2 hours. The mixture was evaporated and the residue was purified by column chromatography on silica using increasingly polar mixtures of methylene chloride and ethyl acetate as eluent. There was thus obtained 4-chloro-6-(2-chloroethoxy)-7-methoxyquinazoline as a white solid (1.06 g); NMR Spectrum: (CDCl$_3$) 3.95 (t, 2H), 4.05 (s, 3H), 4.45 (t, 2H), 7.35 (s, 1H), 7.4 (s, 1H), 8.9 (s, 1H).

EXAMPLE 8

6-(3-chloropropoxy)-4-(5-chloro-2,3-methylenedioxypyrid-4-ylamino)-7-methoxyquinazoline Using an analogous procedure to that described in Example 1, 4-chloro-6-(3-chloropropoxy)-7-methoxyquinazoline was reacted with 4-amino-5-chloro-2,3-methylenedioxypyridine to give the title compound in 58% yield; NMR Spectrum: (CDCl$_3$) 2.4 (m, 2H), 3.8 (t, 2H), 4.05 (s, 3H), 4.35 (t, 2H), 6.15 (s, 2H), 7.05 (s, 1H), 7.2 (s, 1H), 7.3 (s, 1H), 7.75 (s, 1H), 8.7 (s, 1H); Mass Spectrum: M+H$^+$ 423 and 425.

The 4-chloro-6-(3-chloropropoxy)-7-methoxyquinazoline used as a starting material was prepared as follows:—

Di-tert-butyl azodicarboxylate (1.84 g) was added portionwise over a few minutes to a stirred mixture of 4-chloro-6-hydroxy-7-methoxyquinazoline (1.2 g), 3-chloropropanol (0.572 ml), triphenylphosphine (2.1 g) and methylene chloride (30 ml) and the reaction mixture was stirred at ambient temperature for 3 hours. The mixture was evaporated and the residue was purified by column chromatography on silica using increasingly polar mixtures of methylene chloride and ethyl acetate as eluent. The material so obtained was triturated under diethyl ether. The resultant solid was isolated and dried under vacuum. There was thus obtained 4-chloro-6-(3-chloropropoxy)-7-methoxyquinazoline as a white solid (0.84 g); NMR Spectrum: (CDCl$_3$) 2.4 (m, 2H), 3.8 (t, 2H), 4.05 (s, 3H), 4.35 (t, 2H), 7.35 (s, 1H), 7.45 (s, 1H), 8.9 (s, 1H).

EXAMPLE 9

4-(5-chloro-2,3-methylenedioxypyrid-4-ylamino)-7-(3-chloropropoxy)-5-tetrahydropyran-4-yloxyquinazoline Using an analogous procedure to that described in Example 1, 4-chloro-7-(3-chloropropoxy)-5-tetrahydropyran-4-yloxyquinazoline was reacted with 4-amino-5-chloro-2,3-methylenedioxypyridine to give the title compound in 78% yield; Mass Spectrum: M+H$^+$ 493 and 495.

The 4-chloro-7-(3-chloropropoxy)-5-tetrahydropyran-4-yloxyquinazoline used as a starting material was prepared as follows:—

Using an analogous procedure to that described in the portion of Example 4 that is concerned with the preparation of starting materials, 4-chloro-7-hydroxy-5-tetrahydropyran-4-yloxyquinazoline (2.5 g) was reacted with 3-chloropropanol. There was thus obtained the required starting material in 21% yield; NMR Spectrum: (DMSOd$_6$ and CF$_3$CO$_2$D) 1.7 (m, 2H), 2.0 (m, 2H), 2.25 (m, 2H), 3.55 (m, 2H), 3.8 (t, 2H), 3.9 (m, 2H), 4.3 (t, 2H), 4.95 (m, 1H), 6.8 (s, 1H), 6.9 (s, 1H), 9.2 (s, 1H).

EXAMPLE 10

4-(5-chloro-2,3-methylenedioxypyrid-4-ylamino)-7-(2,4-dimethoxybenzyloxy)-5-isopropoxyquinazoline Using an analogous procedure to that described in Example 1, 4-chloro-7-(2,4-dimethoxybenzyloxy)-5-isopropoxyquinazoline was reacted with 4-amino-5-chloro-2,3-methylenedioxypyridine to give the title compound in 75% yield; NMR Spectrum: (CDCl$_3$) 1.55 (d, 6H), 3.8 (s, 3H), 3.85 (s, 3H), 4.8 (m, 1H), 5.15 (s, 2H), 6.15 (s, 2H), 6.5 (m, 2H), 6.6 (s, 1H), 7.0 (s, 1H), 7.35 (d, 1H), 7.75 (s, 1H), 8.6 (s, 1H), 9.6 (s, 1H); Mass Spectrum: M+H$^+$ 525 and 527.

The 4-chloro-7-(2,4-dimethoxybenzyloxy)-5-isopropoxyquinazoline used as a starting material was prepared as follows:—

Sodium hydride (60% dispersion in mineral oil; 40 g) was added portionwise to a solution of isopropanol (30 g) in DMF (500 ml) that had been cooled to 5° C. The mixture was allowed to warm to ambient temperature and was stirred for 60 minutes. 5,7-Difluoro-3,4-dihydroquinazolin-4-one (International Patent Application WO 01/94341; 90 g) was added and the mixture was stirred at ambient temperature for 3 hours. The mixture was poured into water (1 liter) and, with vigorous stirring, glacial acetic acid was added to acidify the mixture to pH5. The resultant solid was isolated, washed with water and with diethyl ether and dried under vacuum. There was thus obtained 7-fluoro-5-isopropoxy-3,4-dihydroquinazolin-4-one (79 g); NMR Spectrum: (DMSOd$_6$) 1.31 (s, 6H), 4.73 (m, 1H), 6.89 (m, 1H), 6.95 (m, 1H), 7.96 (s, 1H); Mass Spectrum: M+H$^+$ 223.

A mixture of 7-fluoro-5-isopropoxy-3,4-dihydroquinazolin-4-one (61 g), 2,4-dimethoxybenzyl alcohol (138 g), potassium tert-butoxide (185 g) and THF (1.5 liters) was stirred and heated to reflux for 18 hours. After cooling, the solvent was evaporated and a mixture of methylene chloride (400 ml) and water (600 ml) was added. With cooling, the 2-phase mixture was neutralised by the addition of 2N aqueous hydrochloric acid. The mixture was filtered and the organic phase was separated, dried over magnesium sulphate and evaporated. The residue was triturated under diethyl ether. There was thus obtained 7-(2,4-dimethoxybenzyloxy)-5-isopropoxy-3,4-dihydroquinazolin-4-one (68 g); NMR Spectrum:

(DMSOd$_6$) 1.28 (s, 6H), 3.78 (s, 3H), 3.82 (s, 3H), 4.63 (m, 1H), 5.06 (s, 2H), 6.55 (m, 2H), 6.62 (s, 1H), 6.71 (s, 1H), 7.33 (d, 1H), 7.88 (s, 1H); Mass Spectrum: M+H$^+$ 371.

A mixture of a portion (4 g) of the material so obtained, phosphorus oxychloride (1.98 g), diisopropylethylamine (3.6 g) and methylene chloride (100 ml) was stirred and heated to 75° C. for 3 hours. The mixture was cooled and evaporated. The residue was dried under vacuum for 1 hour and purified by column chromatography on silica using a 20:3 mixture of methylene chloride and ethyl acetate as eluent. There was thus obtained 4-chloro-7-(2,4-dimethoxybenzyloxy)-5 isopropoxyquinazoline as a solid (2.63 g); NMR Spectrum: (CDCl$_3$) 1.46 (s, 3H), 1.47 (s, 3H), 3.83 (s, 3H), 3.85 (s, 3H), 4.68 (m, 1H), 5.16 (s, 2H), 6.52 (m, 2), 6.65 (s, 1H), 7.06 (s, 1H), 7.33 (d, 1H), 8.78 (s, 1H); Mass Spectrum: M+H$^+$ 389.

EXAMPLE 11

4-(5-chloro-2,3-methylenedioxypyrid-4-ylamino)-7-hydroxy-5-isopropoxyquinazoline Trifluoroacetic acid (4.5 ml) was added to a solution of 4-(5-chloro-2,3-methylenedioxypyrid-4-ylamino)-7-(2,4-dimethoxybenzyloxy)-5-isopropoxyquinazoline (0.53 g) in methylene chloride (9 ml) and the reaction mixture was stirred at ambient temperature for 30 minutes. The solvents were evaporated to give the di-trifluoroacetic acid salt (0.618 g) of the required compound. A portion of this salt was dissolved in methylene chloride (2 ml) and a 7M methanolic ammonia solution was added. The mixture was filtered and the filtrate was evaporated. There was thus obtained the title compound; Mass Spectrum: M+H$^+$ 375 and 377.

EXAMPLE 12

4-(5-chloro-2,3-methylenedioxypyrid-4-ylamino)-7-(3-chloropropoxy)-5-isopropoxyquinazoline A mixture of 4-(5-chloro-2,3-methylenedioxypyrid-4-ylamino)-7-hydroxy-5-isopropoxyquinazoline di-trifluoroacetic acid salt (0.615 g), 1,3-dichloropropane (0.38 ml), potassium carbonate (0.56 g) and DMF (6 ml) was stirred and heated to 80° C. for 5 hours. After cooling, the solids were filtered off and the filtrate was evaporated. The residue was purified by column chromatography on silica using a 24:1 mixture of methylene chloride and methanol as eluent. There was thus obtained the title compound (0.32 g); NMR Spectrum: (CDCl$_3$) 1.55 (d, 6H), 2.3 (m, 2H), 3.8 (t, 2H), 4.25 (t, 2H), 4.9 (m, 1H), 6.15 (s, 2H), 6.5 (s, 1H), 6.9 (s, 1H), 7.75 (s, 1H), 8.6 (s, 1H), 9.6 (s, 1H).

EXAMPLE 13

4-(5-chloro-2,3-methylenedioxypyrid-4-ylamino)-7-(3-chloropropoxy)quinazoline

Using an analogous procedure to that described in Example 1, 4-chloro-7-(3-chloropropoxy)quinazoline was reacted with 4-amino-5-chloro-2,3-methylenedioxypyridine to give the title compound in 89% yield; NMR Spectrum: (DMSOd$_6$ and CF$_3$CO$_2$D) 2.25 (m, 2H), 3.8 (t, 2H), 4.35 (t, 2H), 6.25 (s, 2H), 7.35 (s, 1H), 7.6 (d, 1H), 7.9 (s, 1H), 8.7 (d, 1H), 9.0 (s, 1H).

The 4-chloro-7-(3-chloropropoxy)quinazoline used as a starting material was prepared as follows:—

Sodium hydride (60% dispersion in mineral oil; 2.92 g) was added portionwise over 45 minutes to a stirred mixture of 1,3-propanediol (5.3 ml) and DMF (20 ml) that had been cooled to 0° C. The resultant mixture was stirred at ambient temperature for 1 hour and then heated to 60° C. 7-Fluoro-3,4-dihydroquinazolin-4-one (International Patent Application WO 01/04102, Example 2, Note [12] thereof; 2 g) was added and the reaction mixture was stirred and heated to 115° C. for 3.5 hours. The reaction mixture was cooled to 0° C. and water (50 ml) was added. The mixture was acidified to pH5.9 with 2N aqueous hydrochloric acid. The resultant precipitate was collected by filtration, washed with water and dried under vacuum over phosphorus pentoxide at 40° C. The solid so obtained was washed with diethyl ether and dried again under vacuum. There was thus obtained 7-(3-hydroxypropoxy)-3,4-dihydroquinazolin-4-one (2.1 g); NMR Spectrum: (DMSOd$_6$) 1.9 (m, 2H), 3.6 (m, 2H), 4.15 (m, 2H), 4.6 (br s, 2H), 7.1 (m, 2H, 8.05 (m, 2H); Mass Spectrum: M+H$^+$ 221.

A mixture of 7-(3-hydroxypropoxy)-3,4-dihydroquinazolin-4-one (1 g), 1,2-dichloroethane (50 ml), triphenylphosphine (5.24 g) and carbon tetrachloride (2.9 ml) was stirred and heated to 70° C. for 2 hours. The solvent was evaporated and the residue was purified by column chromatography on silica using initially methylene chloride followed by gradually increasing the polarity of the solvent up to a 9:1 mixture of methylene chloride and methanol as eluent. There was thus obtained 4-chloro-7-(3-chloropropoxy)quinazoline (1.23 g; containing 0.6 mole of triphenylphosphine oxide per mole of product); Mass Spectrum: M+H$^+$ 393 and 395.

EXAMPLE 14

7-(2-chloroethoxy)-4-(2,3-methylenedioxypyrid-4-ylamino)-6-methoxyquinazoline

Sodium hexamethyldisilazane (1M solution in THF; 2 ml) was added dropwise to a mixture of 4-amino-2,3-methylenedioxypyridine (0.138 g), 4-chloro-7-(2-chloroethoxy)-6-methoxyquinazoline (0.272 g) and THF (5 ml) that had been cooled to 0° C. The mixture was stirred at 0° C. for 1 hour. The resultant mixture was allowed to warm to ambient temperature and was stirred for 2 hours. The reaction was quenched by the addition of glacial acetic acid (0.12 ml). The solvents were evaporated and the residue was partitioned between methylene chloride and an aqueous ammonium hydroxide solution. The organic layer was collected and concentrated to a small volume. Diethyl ether was added and a precipitate formed. The resultant solid was isolated, washed with diethyl ether and dried. There was thus obtained the title compound (0.245 g); NMR Spectrum: (DMSOd$_6$) 3.97 (s, 3H), 4.04 (m, 2H), 4.45 (m, 2H), 6.12 (s, 2H), 7.13 (br d, 1H), 7.25 (s, 1H), 7.60 (d, 1H), 7.83 (s, 1H), 8.47 (s, 1H), 9.87 (br s, 1H); Mass Spectrum: M+H$^+$ 375.

The 4-amino-2,3-methylenedioxypyridine used as a starting material was prepared as follows:—

Dibromomethane (31.5 ml) was added to a mixture 2,3-dihydroxypyridine (33 g), potassium carbonate (62 g) and NMP (200 ml) and the mixture was stirred and heated to 90° C. for 16 hours. The mixture was cooled to ambient temperature and filtered. The filtrate was partitioned between diethyl ether (5×100 ml) and water (200 ml). The organic extracts were combined and concentrated under vacuum to a volume of about 20 ml. Petroleum ether (b.p 40-60° C.; 300 ml) was added and the solution was washed with brine. The organic layer was separated and evaporated. There was thus obtained 2,3-methylenedioxypyridine as a liquid (5.1 g); NMR Spectrum: (CDCl$_3$) 6.05 (s, 2H), 6.76 (m, 1H), 6.99 (d, 1H), 7.65 (d, 1H).

Using an analogous procedure to that described in the second paragraph of the portion of Example 1 that is concerned with the preparation of the starting material 4-amino-5-chloro-2,3-methylenedioxypyridine, 2,3-methylenedioxypyridine was reacted with carbon dioxide gas to give 2,3-methylenedioxypyridine-4-carboxylic acid in 80% yield; NMR Spectrum: (DMSOd$_6$) 6.24 (s, 2H), 7.13 (d, 1H); 7.63 (d, 1H).

Using an analogous procedure to that described in the third paragraph of that portion of Example 1 that is concerned with the preparation of starting materials, 2,3-methylenedioxypyridin-4-carboxylic acid was reacted with diphenylphosphoryl azide and anhydrous tert-butanol to give tert-butyl 2,3-methylenedioxypyrid-4-ylcarbamate in 62% yield; Mass Spectrum: M+H$^+$ 239.

Using an analogous procedure to that described in the last paragraph of that portion of Example 1 that is concerned with the preparation of starting materials, tert-butyl 2,3-methylenedioxypyrid-4-ylcarbamate was reacted with trifluoroacetic acid to give 4-amino-2,3-methylenedioxypyridine in 80% yield; NMR Spectrum: (CDCl$_3$) 3.98 (m, 2H), 5.98 (s, 2H), 6.24 (d, 1H), 7.44 (d, 1H); Mass Spectrum: M+H$^+$ 139.

EXAMPLE 15

7-(3-chloropropoxy)-4-(2,3-methylenedioxypyrid-4-ylamino)-6-methoxyquinazoline Using an analogous procedure to that described in Example 14, 4-chloro-7-(3-chloropropoxy)-6-methoxyquinazoline was reacted with 4-amino-2,3-methylenedioxypyridine to give the title compound in 68% yield; NMR Spectrum: (DMSOd$_6$) 2.26 (m, 2H), 3.83 (m, 2H), 3.96 (s, 3H), 4.28 (m, 2H), 6.12 (s, 2H), 7.15 (br d, 1H), 7.25 (s, 1H), 7.61 (d, 1H), 7.81 (s, 1H), 8.49 (s, 1H), 9.79 (br s, 1H); Mass Spectrum: M+H$^+$ 389.

EXAMPLE 16

7-[2-(4-acetylpiperazin-1-yl)ethoxy]-4-(2,3-methylenedioxypyrid-4-ylamino)-5-tetrahydropyran-4-yloxyquinazoline Using an analogous procedure to that described in Example 1, 7-[2-(4-acetylpiperazin-1-yl)ethoxy]chloro-5-tetrahydropyran-4-yloxyquinazoline (0.113 g) was reacted with 4-amino-2,3-methylenedioxypyridine (0.036 g). The reaction mixture was quenched with glacial acetic acid (0.031 g) and diluted with methanol. The mixture was evaporated and the residue was purified by column chromatography on a C18 reversed phase silica column (Waters Symmetry column, 5 microns silica, 20 mm diameter, 100 mm length) using a decreasingly polar mixture of water and acetonitrile (containing 1% acetic acid) as eluent. The material so obtained was diluted with a 7M methanolic ammonia solution. The mixture was evaporated and the material so obtained was dissolved in methylene chloride. The solution was dried over magnesium sulphate and evaporated to give the title compound as a foam in 53% yield; NMR Spectrum: (CDCl$_3$) 2.02 (m, 2H), 2.1 (s, 3H), 2.22 (m, 2H), 2.6 (m, 4H), 2.9 (m, 2H), 3.51 (m, 2H), 3.6 (m, 2H), 3.66 (m, 2H), 4.1 (m, 2H), 4.25 (m, 2H), 4.73 (m, 1H), 6.13 (s, 2H), 6.59 (s, 1H), 6.9 (s, 1H), 7.7 (d, 1H), 8.36 (d, 1H), 8.66 (s, 1H); Mass Spectrum: M+H$^+$ 537.

The 7-[2-(4-acetylpiperazin-1-yl)ethoxy]-4-chloro-5-tetrahydropyran-4-yloxyquinazoline used as a starting material was prepared as follows:—

Sodium hydride (60% dispersion in mineral oil; 0.6 g) was added portionwise to a solution of 4-hydroxytetrahydropyran (0.78 g) in DMF (10 ml) that had been cooled to 5° C. The mixture was allowed to warm to ambient temperature and was stirred for 15 minutes. 5,7-Difluoro-3,4-dihydroquinazolin-4-one (International Patent Application WO 01/94341; 0.9 g) was added and the mixture was stirred at ambient temperature for 30 minutes. The mixture was poured into water (100 ml) and, with vigorous stirring, glacial acetic acid was added to acidify the mixture to pH5. The resultant solid was isolated, washed with water and with diethyl ether and dried under vacuum. There was thus obtained 7-fluoro-5-tetrahydropyran-4-yloxy-3,4-dihydroquinazolin-4-one (1.1 g); NMR Spectrum: (DMSOd$_6$) 1.6-1.75 (m, 2H), 1.9-2.0 (m, 2H), 3.5-3.6 (m, 2H), 3.85-3.95 (m, 2H), 4.8 (m, 1H), 6.9 (m, 1H), 7.05 (m, 1H), 8.0 (s, 1H); Mass Spectrum: M+H$^+$ 265.

After repetition of the prior reaction, a mixture of 7-fluoro-5-tetrahydropyran-4-yloxy-3,4-dihydroquinazolin-4-one (5.3 g), 2-piperazin-1-ylethanol (3.9 g), potassium tert-butoxide (6.7 g) and THF (200 ml) was stirred and heated to reflux for 3 hours. A second portion (6.7 g) of potassium tert-butoxide was added and the mixture was heated to reflux for a further 12 hours. The mixture was cooled to ambient temperature and filtered. The filtrate was evaporated and the residue was purified by column chromatography on silica using increasingly polar mixtures of methylene chloride and a 7M methanolic ammonia solution as eluent. The material so obtained was triturated under diethyl ether. There was thus obtained 7-(2-piperazin-1-ylethoxy)-5-tetrahydropyran-4-yloxy-3,4-dihydroquinazolin-4-one (5.2 g); NMR Spectrum: (DMSOd$_6$ and CF$_3$CO$_2$D) 1.75 (m, 2H), 2.03 (m, 2H), 3.2-4.0 (m, 14H), 4.59 (m, 2H), 4.92 (m, 1H), 6.88 (s, 1H), 6.9 (s, 1H), 9.28 (s, 1H); Mass Spectrum: M+H$^+$ 375.

Acetic anhydride (1.51 ml) was added dropwise to a stirred mixture of 7-(2-piperazin-1-ylethoxy)-5-tetrahydropyran-4-yloxy-3,4-dihydroquinazolin-4-one (5 g) and water (20 ml) and the resultant mixture was stirred at ambient temperature for 10 minutes. The reaction mixture was evaporated and the residue was triturated under diethyl ether. The resultant solid was isolated, washed with diethyl ether and dried under vacuum. There was thus obtained 7-[2-(4-acetylpiperazin-1-yl)ethoxy]-5-tetrahydropyran-4-yloxy-3,4-dihydroquinazolin-4-one (5.5 g); NMR Spectrum: (DMSOd$_6$ and CF$_3$CO$_2$D) 1.75 (m, 2H), 2.03 (m, 2H), 2.08 (s, 3H), 3.0-4.2 (m, 13H), 4.56 (m, 3H), 4.94 (m, 1H), 6.84 (s, 1H), 6.9 (s, 1H), 9.21 (s, 1H); Mass Spectrum: M+H$^+$ 417.

A mixture of a portion (0.416 g) of the material so obtained, triphenylphosphine (0.655 g), carbon tetrachloride (0.34 ml) and 1,2-dichloroethane (20 ml) was stirred and heated to 70° C. for 1.5 hours. The mixture was evaporated and the residue was purified by column chromatography on silica using increasingly polar mixtures of methylene chloride and a 7M methanolic ammonia solution (a solvent gradient having from 1% to 3% methanolic ammonia solution) as eluent. There was thus obtained 7-[2-(4-acetylpiperazin-1-yl)ethoxy]-4-chloro-5-tetrahydropyran-4-yloxyquinazoline as a solid (0.35 g); NMR Spectrum: (CDCl$_3$) 2.0 (m, 2H), 2.1 (s, 3H), 2.12 (m, 2H), 2.58 (m, 4H), 2.9 (m, 2H), 3.51 (m, 2H), 3.68 (m, 4H), 4.05 (m, 2H), 4.25 (m, 2H), 4.75 (m, 1H), 6.62 (s, 1H), 6.94 (s, 1H), 8.82 (s, 1H); Mass Spectrum: M+H$^+$ 435 and 437.

EXAMPLE 17

7-[2-(4-acetylpiperazin-1-yl)ethoxy]-4-(2,3-methylenedioxypyrid-4-ylamino)-5-isopropoxyquinazoline Using an analogous procedure to that described in Example 16, 7-[2-(4-acetylpiperazin-1-yl)ethoxy]-4-chloro-5-isopropoxyquinazoline was reacted with 4-amino-2,3-methylenedioxypyridine to give the title compound in 55% yield; NMR Spectrum: (CDCl$_3$) 1.55 (s, 3H), 1.56 (s, 3H), 2.1 (s, 3H), 2.59 (m, 4H), 2.89 (m, 2H), 3.51 (m, 2H), 3.67 (m, 2H), 4.24 (m, 2H), 4.85 (m, 1H), 6.13 (s, 2H), 6.57 (s, 1H), 6.85 (s, 1H), 7.71 (d, 1H), 8.41 (d, 1H), 8.66 (s, 1H); Mass Spectrum: M+H$^+$ 495.

The 7-[2-(4-acetylpiperazin-1-yl)ethoxy]-4-chloro-5-isopropoxyquinazoline that is required as a starting material was prepared as follows using analogous procedures to those described in the portion of Example 16 that is concerned with the preparation of starting materials.

5,7-Difluoro-3,4-dihydroquinazolin-4-one was reacted with isopropanol to give 7-fluoro-5-isopropoxy-3,4-dihydroquinazolin-4-one in 73% yield; NMR Spectrum: (DMSOd$_6$) 1.31 (s, 6H), 4.73 (m, 1H), 6.89 (m, 1H), 6.95 (m, 1H), 7.96 (s, 1H); Mass Spectrum: M+H$^+$ 223.

The material so obtained was reacted with 2-piperazin-1-ylethanol to give 5-isopropoxy-7-(2-piperazin-1-ylethoxy)-3,4-dihydroquinazolin-4-one in 63% yield; NMR Spectrum: (CDCl$_3$) 1.45 (s, 3H), 1.46 (s, 3H), 2.4-3.0 (m, 10H), 4.2 (t, 2H), 4.62 (m, 1H), 6.51 (s, 1H), 6.72 (s, 1H), 7.9 (s, 1H).

The material so obtained was reacted with an excess of acetic anhydride but using methylene chloride rather than water as the reaction solvent. The reaction mixture was stirred at ambient temperature for 15 minutes. The mixture was partitioned between methylene chloride and a saturated aqueous sodium bicarbonate solution. The organic layer was washed with water and with brine, dried over magnesium sulphate and evaporated. The residue was triturated under a mixture of acetonitrile and diethyl ether. There was thus obtained 7-[2-(4-acetylpiperazin-1-yl)ethoxy]-5-isopropoxy-3,4-dihydroquinazolin-4-one in 70% yield; NMR Spectrum: (CDCl$_3$) 1.46 (s, 3H), 1.47 (s, 3H), 2.1 (s, 3H), 2.58 (m, 4H), 2.87 (t, 2H), 3.5 (m, 2H), 3.66 (m, 2H), 4.21 (t, 2H), 4.63 (m, 1H), 6.51 (s, 1H), 6.72 (s, 1H), 7.9 (s, 1H), 9.9 (br s, 1H); Mass Spectrum: M+H$^+$ 375.

The material so obtained was reacted with carbon tetrachloride and triphenylphosphine to give 7-[2-(4-acetylpiperazin-1-yl)ethoxy]-4-chloro-5-isopropoxyquinazoline in 68% yield which was used without further purification.

EXAMPLE 18

4-(5-chloro-2,3-methylenedioxypyrid-4-ylamino)-7-{2-[4-(2-dimethylaminoacetyl)piperazin-1-yl]ethoxy}-5-isopropoxyquinazoline 4-(5-Chloro-2,3-methylenedioxypyrid-4-ylamino)-5-isopropoxy-7-(2-piperazin-1-ylethoxy)quinazoline (0.2 g) was added to a stirred mixture of 2-dimethylaminoacetyl chloride hydrochloride (0.097 g), triethylamine (0.15 ml) and methylene chloride (5 ml) that had been cooled to 0° C. The reaction mixture was allowed to warm to ambient temperature and stirred for 2 hours. A second portion of each of 2-dimethylaminoacetyl chloride hydrochloride (0.097 g) and triethylamine (0.057 ml) were added and the reaction was stirred at ambient temperature for 16 hours overnight. Methylene chloride (50 ml) was added and the reaction mixture was extracted twice with a saturated aqueous sodium bicarbonate solution. The organic phase was dried over magnesium sulphate and evaporated. The residue was purified by column chromatography on silica using increasingly polar solvent mixtures, starting with a 9:1 mixture of methylene chloride and methanol and ending with a 90:8:2 mixture of methylene chloride, methanol and a saturated methanolic ammonia solution. There was thus obtained the title compound as a foam (0.155 g); NMR Spectrum: (CDCl$_3$) 1.55 (d, 6H), 2.3 (s, 6H), 2.6 (m, 4H), 2.9 (t, 2H), 3.1 (s, 2H), 3.65 (m, 4H), 4.25 (t, 2H), 4.85 (s, 1H), 6.15 (s, 2H), 6.55 (s, 1H), 6.85 (s, 1H), 7.75 (s, 1H), 8.6 (s, 1H), 9.6 (s, 1H); Mass Spectrum: M+H$^+$ 572 and 574; Elemental Analysis: Found C, 55.1; H, 6.1; N, 16.8; C$_{27}$H$_{34}$ClN$_7$O$_5$ 0.75H$_2$O requires C, 55.4; H, 6.1; N, 16.7%.

EXAMPLE 19

7-(N-tert-butoxycarbonylpiperidin-4-ylmethoxy)-4-(5-chloro-2,3-methylenedioxypyrid-4-ylamino)-6-methoxyquinazoline Using a similar procedure to that described in Example 1, a solution of 4-amino-5-chloro-2,3-methylenedioxypyridine (0.193 g) in DMF (2 ml) was added to a stirred suspension of sodium hydride (60% dispersion in mineral oil, 0.048 g) in DMF (2 ml) and the mixture was stirred at ambient temperature for 15 minutes. A solution of 7-(N-tert-butoxycarbonylpiperidin-4-ylmethoxy)-4-chloro-6-methoxyquinazoline [International Patent Application WO 02/16352 (Note [24] within Example 2 thereof; 0.38 g] in DMF (4 ml) was added and the resultant mixture was stirred at ambient temperature for 1 hour. The reaction mixture was partitioned between ethyl acetate and brine. The organic phase was dried over magnesium sulphate and evaporated. The residue was purified by column chromatography on silica using a 49:1 mixture of methylene chloride and methanol. There was thus obtained the title compound as a solid (0.24 g); NMR Spectrum: DMSOd$_6$) 1.29 (m, 2H), 1.45 (s, 9H), 1.8 (m, 2H), 2.04 (m, 1H), 2.83 (m, 2H), 4.0 (m, 7H), 8.12 (br s, 2H), 7.17 (br s, 1H), 7.72 (m, 2H), 8.37 (br s, 1H), 9.37 (br s, 1H); Mass Spectrum: M+H$^+$ 544 and 546.

EXAMPLE 20

4-(5-chloro-2,3-methylenedioxypyrid-4-ylamino)-6-methoxy 7-(piperidin-4-ylmethoxy)quinazoline Trifluoroacetic acid (1 ml) was added to a solution of 7-(N-tert-butoxycarbonylpiperidin-4-ylmethoxy)-4-(5-chloro-2,3-methylenedioxypyrid-4-ylamino)-6-methoxyquinazoline (0.253 g) in methylene chloride (10 ml) and the reaction mixture was stirred at ambient temperature for 1 hour. The reaction mixture was evaporated. Toluene was added to the residue and the mixture was evaporated. The residue was purified by column chromatography on silica (Isolute SCX column) using a 7M methanolic ammonia solution as eluent. There was thus obtained the title compound as a solid (0.187 g); NMR Spectrum: (DMSOd$_6$) 1.25 (m, 2H), 1.75 (d, 2H), 1.93 (m, 1H), 2.54 (m, 2H), 3.0 (d, 2H), 3.93 (s, 3H), 3.98 (d, 2H), 6.17 (s, 2H), 7.15 (s, 1H), 7.76 (s, 1H), 7.78 (s, 1H), 8.23 (s, 1H); Mass Spectrum: M+H$^+$ 444 and 446.

EXAMPLE 21

4-(5-chloro-2,3-methylenedioxypyrid-4-ylamino)-7-[N-(2-dimethylaminoacetyl)piperidin-4-ylmethoxy]-6-methoxyquinazoline Diisopropylethylamine (0.118 ml) was added to a mixture of 4-(5-chloro-2,3-methylenedioxypyrid-4-ylamino)-6-methoxy-7-(piperidin-4-ylmethoxy)quinazoline (0.15 g), N,N-dimethylglycine (0.042 g), 2-(7-azabenzotriazol-1-yl)-1,1,3,3-tetramethyluronium hexafluorophosphate(V) (0.154 g) and DMF (3 ml) and the reaction mixture was stirred at ambient temperature for 16 hours. The mixture was diluted with ethyl acetate and washed with brine. The organic solution was dried over magnesium sulphate and evaporated. The residue was purified by column chromatography on silica using a 100:3 mixture of methylene chloride and a 7M methanolic ammonia solution as eluent. There was thus obtained the title compound as a solid (0.051 g); NMR Spectrum: (DMSOd$_6$) 1.11-1.36 (m, 2H), 1.83 (d, 2H), 2.11 (m, 1H), 2.19 (s, 6H), 2.61 (t, 1H), 3.03 (m, 2H), 3.12 (d, 1H), 3.93 (s, 3H), 4.06 (m, 3H), 4.4 (d, 1H), 6.19 (br s, 2H), 7.19 (brs, 1H), 7.78 (m, 2H), 8.39 (br s, 1H), 9.71 (br s, 1H); Mass Spectrum: M+H$^+$ 529 and 531.

EXAMPLE 22

7-[2-(4-acetylpiperazin-1-yl)ethoxy]-4-(5-chloro-2,3-methylenedioxypyrid-4-ylamino)-5-isopropoxyquinazoline A mixture of 7-(2-chloroethoxy)-4-(5-chloro-2,3-methylenedioxypyrid-4-ylamino)-5-isopropoxyquinazoline (24 g), 1-acetylpiperazine (21 g), potassium iodide (18 g) and DMA (500 ml) was stirred and heated to 100° C. for 4 hours. The solvent was evaporated and the residue was partitioned between methylene chloride (1 liter) and water (500 ml). The aqueous layer was extracted with methylene chloride. The organic solutions were combined, washed with brine, dried over magnesium sulphate and evaporated. The residue was purified by column chromatography on silica using increasingly polar mixtures of methylene chloride and methanol (from a 20:1 mixture to a 10:1 mixture) as eluent. After evaporation of the solvent, the material so obtained was triturated under diethyl ether. There was thus obtained the title compound as a white solid (26.2 g); m.p. 208-210° C.

The 7-(2-chloroethoxy)-4-(5-chloro-2,3-methylenedioxypyrid-4-ylamino)-5-isopropoxyquinazoline used as a starting material was obtained as follows:—

Sodium hexamethyldisilazane (1M solution in THF, 164 ml) was added dropwise over one hour to a ice-cooled mixture of 4-chloro-7-(2,4-dimethoxybenzyloxy)-5-isopropoxyquinazoline (32 g), 4-amino-5-chloro-2,3-methylenedioxypyridine (15.6 g) and THF (430 ml) whilst maintaining the temperature of the reaction mixture at about 3° C. At the end of the addition, the reaction mixture was allowed to warm to ambient temperature and was stirred for 2.5 hours. The reaction mixture was cooled to 0° C. and a mixture of acetic acid (9.4 ml) and water (250 ml) was added. The mixture was evaporated and the residue was partitioned between methylene chloride and water, the basicity of the aqueous phase having been adjusted to 7.5 by the addition of 3N aqueous hydrochloric acid solution. The organic phase was separated and the aqueous phase was extracted three times with methylene chloride. The organic layers were combined, washed with brine, dried over magnesium sulphate and evaporated. The resultant solid was triturated under ethyl acetate. There was thus obtained 4-(5-chloro-2,3-methylenedioxypyrid-4-ylamino)-7-(2,4-dimethoxybenzyloxy)-5-isopropoxyquinazoline as a white solid (38 g); Mass Spectrum: M+H$^+$ 525 and 527.

Triethylsilane (70 ml) and trifluoroacetic acid (48 ml) were added in turn to an ice-cooled solution of 4-(5-chloro-2,3-methylenedioxypyrid-4-ylamino)-7-(2,4-dimethoxybenzyloxy)-5-isopropoxyquinazoline (37.7 g) in methylene chloride (560 ml) and the resultant reaction mixture was stirred at ambient temperature for 1 hour. The solvents were evaporated under high vacuum. The resultant solid was triturated under ethyl acetate. The material so obtained was isolated, washed with ethyl acetate and dried under high vacuum. There was thus obtained the di-trifluoroacetic acid salt (37.4 g) of 4-(5-chloro-2,3-methylenedioxypyrid-4-ylamino)-7-hydroxy-5-isopropoxyquinazoline which was used without further purification.

Potassium carbonate (34.6 g) was added to a mixture of 4-(5-chloro-2,3-methylenedioxypyrid-4-ylamino)-7-hydroxy-5-isopropoxyquinazoline di-trifluoroacetic acid salt (49 g), 1,2-dichloroethane (440 ml) and DMF (245 ml) and the mixture was stirred and heated to 90° C. for 3.5 hours. An additional portion (7 g) of potassium carbonate was added and the mixture was stirred at 90° C. for a further hour. The reaction mixture was cooled to ambient temperature and the solids were filtered off and washed with methylene chloride. The filtrate and washings were combined and evaporated. The resultant residue was purified by column chromatography on silica using increasingly polar mixtures of methylene chloride and methanol (from a 50:1 mixture to a 20:1 mixture) as eluent. There was thus obtained 7-(2-chloroethoxy)-4-(5-chloro-2,3-methylenedioxypyrid-4-ylamino)-5-isopropoxyquinazoline as a white solid (37.1 g); Mass Spectrum: M+H$^+$ 437 and 439.

The invention claimed is:

1. A quinazoline derivative selected from:
   7-[2-(4-acetylpiperazin-1-yl)ethoxy]-4-(5-chloro-2,3-methylenedioxypyrid-4-ylamino)-5-tetrahydropyran-4-yloxyquinazoline,
   4-(5-chloro-2,3-methylenedioxypyrid-4-ylamino)-7-{2-[(3RS,4SR)-3,4-methylenedioxypyrrolidin-1-yl]ethoxy}-5-tetrahydropyran-4-yloxyquinazoline,
   4-(5-chloro-2,3-methylenedioxypyrid-4-ylamino)-7-[2-(4-prop-2-ynylpiperazin-1-yl)ethoxy]-5-tetrahydropyran-4-yloxyquinazoline,
   4-(5-chloro-2,3-methylenedioxypyrid-4-ylamino-7-[3-(4-prop-2-ynylpiperazin-1-yl)propoxy]-5-tetrahydropyran-4-yloxyquinazoline,
   4-(5-chloro-2,3-methylenedioxypyrid-4-ylamino)-7-(2-morpholinoethoxy)-5-tetrahydropyran-4-yloxyquinazoline and
   4-(5-chloro-2,3-methylenedioxypyrid-4-ylamino)-7-(3-morpholinopropoxy)-5-tetrahydropyran-4-yloxyquinazoline;
   or a pharmaceutically-acceptable acid-addition salt thereof.

2. A quinazoline derivative selected from:
   7-[2-(4-acetylpiperazin-1-yl)ethoxy]-4-(5-chloro-2,3-methylenedioxypyrid-4-ylamino)-5-isopropoxyquinazoline,
   4-(5-chloro-2,3-methylenedioxypyrid-4-ylamino)-5-isopropoxy-7-(2-piperazin-1-ylethoxy)quinazoline,
   4-(5-chloro-2,3-methylenedioxypyrid-4-ylamino)-7-{2-[4-(2-hydroxyethyl)piperazin-1-yl]ethoxy}-5-isopropoxyquinazoline,
   4-(5-chloro-2,3-methylenedioxypyrid-4-ylamino)-5-isopropoxy-7-(2-pyrrolidin-1-ylethoxy)quinazoline,
   4-(5-chloro-2,3-methylenedioxypyrid-4-ylamino)-5-isopropoxy-7-(2-piperidinoethoxy)quinazoline,
   4-(5-chloro-2,3-methylenedioxypyrid-4-ylamino)-5-isopropoxy-7-(2-morpholinoethoxy)quinazoline,
   4-(5-chloro-2,3-methylenedioxypyrid-4-ylamino)-5-isopropoxy-7-(3-morpholinopropoxy)quinazoline,
   4-(5-chloro-2,3-methylenedioxypyrid-4-ylamino)-5-isopropoxy-7-[2-(4-prop-2-ynylpiperazin-1-yl)ethoxy]quinazoline, 4-(5-chloro-2,3-methylenedioxypyrid-4-ylamino)-5-isopropoxy-7-[2-(4-methylpiperazin-1-yl)ethoxy]quinazoline and 4-(5-chloro-2,3-methylenedioxypyrid-4-ylamino)-7-{2-[4-(2-dimethylaminoacetyl)piperazin-1-yl]ethoxy}-5-isopropoxyquinazoline;

or a pharmaceutically-acceptable acid-addition salt thereof.

3. A quinazoline derivative according to claim 1 which is:

7-[2-(4-acetylpiperazin-1-yl)ethoxy]-4-(5-chloro-2,3-methylenedioxypyrid-4-ylamino)-5-tetrahydropyran-4-yloxyquinazoline, or a pharmaceutically-acceptable acid-addition salt thereof.

4. A quinazoline derivative according to claim 1 which is:

4-(5-chloro-2,3-methylenedioxypyrid-4-ylamino)-7-{2-[(3RS,4SR)-3,4-methylenedioxypyrrolidin-1-yl]ethoxy}-5-tetrahydropyran-4-yloxyquinazoline, or a pharmaceutically-acceptable acid-addition salt thereof.

5. A quinazoline derivative according to claim 1 which is:

4-(5-chloro-2,3-methylenedioxypyrid-4-ylamino)-7-[2-(4-prop-2-ynylpiperazin-1-yl)ethoxy]-5-tetrahydropyran-4-yloxyquinazoline, or a pharmaceutically-acceptable acid-addition salt thereof.

6. A quinazoline derivative according to claim 1 which is:

4-(5-chloro-2,3-methylenedioxypyrid-4-ylamino)-7-[3-(4-prop-2-ynylpiperazin-1-yl)propoxy]-5-tetrahydropyran-4-yloxyquinazoline, or a pharmaceutically-acceptable acid-addition salt thereof.

7. A quinazoline derivative according to claim 2 which is:

7-[2-(4-acetylpiperazin-1-yl)ethoxy]-4-(5-chloro-2,3-methylenedioxypyrid-4-ylamino)-5-isopropoxyquinazoline, or a pharmaceutically-acceptable acid-addition salt thereof.

8. A quinazoline derivative according to claim 2 which is:

4-(5-chloro-2,3-methylenedioxypyrid-4-ylamino)-5-isopropoxy-7-(2-piperazin-1-ylethoxy)quinazoline, or a pharmaceutically-acceptable acid-addition salt thereof.

9. A quinazoline derivative according to claim 2 which is:

4-(5-chloro-2,3-methylenedioxypyrid-4-ylamino)-7-{2-[4-(2-hydroxyethyl)piperazin-1-yl]ethoxy}-5-isopropoxyquinazoline, or a pharmaceutically-acceptable acid-addition salt thereof.

10. A quinazoline derivative according to claim 2 which is:

4-(5-chloro-2,3-methylenedioxypyrid-4-ylamino)-5-isopropoxy-7-(2-pyrrolidin-1-ylethoxy)quinazoline, or a pharmaceutically-acceptable acid-addition salt thereof.

11. A quinazoline derivative according to claim 2 which is:

4-(5-chloro-2,3-methylenedioxypyrid-4-ylamino)-5-isopropoxy-7-(2-piperidinoethoxy)quinazoline, or a pharmaceutically-acceptable acid-addition salt thereof.

12. A pharmaceutical composition which comprises a quinazoline derivative of the according to any one of claims 1, 2 and 3-11, or a pharmaceutically-acceptable salt thereof, in association with a pharmaceutically-acceptable diluent or carrier.

* * * * *

UNITED STATES PATENT AND TRADEMARK OFFICE
CERTIFICATE OF CORRECTION

| | | |
|---|---|---|
| PATENT NO. | : 7,462,623 B2 | Page 1 of 1 |
| APPLICATION NO. | : 10/533931 | |
| DATED | : December 9, 2008 | |
| INVENTOR(S) | : Ple | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this

Fifteenth Day of February, 2011

David J. Kappos
*Director of the United States Patent and Trademark Office*